(12) United States Patent
Pellegrino et al.

(10) Patent No.: US 9,039,701 B2
(45) Date of Patent: *May 26, 2015

(54) CHANNELING PATHS INTO BONE

(71) Applicant: Relievant Medsystems, Inc., Redwood City, CA (US)

(72) Inventors: Richard Pellegrino, Ashburn, VA (US); Samit Patel, San Francisco, CA (US); Harold Carrison, Pleasanton, CA (US)

(73) Assignee: Relievant Medsystems, Inc., Redwood City, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 13/963,767

(22) Filed: Aug. 9, 2013

(65) Prior Publication Data

US 2013/0324997 A1 Dec. 5, 2013

Related U.S. Application Data

(60) Continuation of application No. 13/862,242, filed on Apr. 12, 2013, which is a division of application No. 12/566,895, filed on Sep. 25, 2009, now Pat. No. 8,419,730.

(60) Provisional application No. 61/100,553, filed on Sep. 26, 2008.

(51) Int. Cl.
*A61B 18/12* (2006.01)
*A61B 17/56* (2006.01)
(Continued)

(52) U.S. Cl.
CPC ... *A61B 17/3472* (2013.01); *A61B 2018/00339* (2013.01); *A61B 17/8819* (2013.01);
(Continued)

(58) Field of Classification Search
CPC .... A61B 1/317; A61B 5/4504; A61B 5/6878; A61B 10/025; A61B 2017/347; A61B 17/3472; A61B 17/56; A61B 17/809; A61B 2018/00565; A61B 2018/0044; A61B 17/1757; A61B 17/1671; A61B 2018/00339; A61B 17/8819; A61B 18/0206; A61B 18/1492; A61B 18/18; A61B 18/20; A61B 2018/00011; A61B 18/148
USPC .......................... 606/12, 44–46, 92, 297, 185
See application file for complete search history.

(56) References Cited

U.S. PATENT DOCUMENTS 3,845,771 A 11/1974 Vise
3,920,021 A 11/1975 Hiltebrandt
(Continued)

FOREIGN PATENT DOCUMENTS

EP 0040658 12/1981
EP 0584959 3/1994
(Continued)

OTHER PUBLICATIONS

A Novel Approach for Treating Chronic Lower Back Pain, Abstract for Presentation at North American Spine Society 26th Annual Meeting in Chicago, IL on Nov. 4, 2011.
(Continued)

*Primary Examiner* — Jaymi Della
(74) *Attorney, Agent, or Firm* — Knobbe, Martens, Olson & Bear LLP

(57) ABSTRACT

System and methods are shown having a tube-within-tube assembly with a deployable curved deflectable tube or cannula that deploys from a straight cannula or trocar. The curved cannula has a pre-curved distal end to create an angular range of 0° to 180° when fully deployed from the straight trocar. The curve is configured such that the flexible element carrying a treatment device can navigate through the angular range of deployment of the curved cannula. The curved cannula allows the flexible element to navigate through a curve within bone without veering off towards an unintended direction.

20 Claims, 9 Drawing Sheets

(51) Int. Cl.
  *A61B 17/34*   (2006.01)
  *A61B 17/88*   (2006.01)
  *A61B 18/18*   (2006.01)
  *A61B 18/00*   (2006.01)
  *A61B 18/02*   (2006.01)
  *A61B 18/14*   (2006.01)
  *A61B 18/20*   (2006.01)
  *A61N 7/00*   (2006.01)
  *A61N 7/02*   (2006.01)

(52) U.S. Cl.
  CPC ......... *A61B18/0206* (2013.01); *A61B 18/1492* (2013.01); *A61B 18/18* (2013.01); *A61B 18/20* (2013.01); *A61B 2018/00011* (2013.01); *A61B 2018/00017* (2013.01); *A61B 2018/00577* (2013.01); *A61N 2007/0026* (2013.01); *A61N 2007/025* (2013.01); *A61B 18/148* (2013.01)

(56) References Cited

U.S. PATENT DOCUMENTS

| | | |
|---|---|---|
| 4,044,774 A | 8/1977 | Corbin et al. |
| 4,116,198 A | 9/1978 | Roos |
| 4,312,364 A | 1/1982 | Convert et al. |
| 4,448,198 A | 5/1984 | Turner |
| 4,573,448 A | 3/1986 | Kambin |
| 4,657,017 A | 4/1987 | Sorochenko |
| 4,679,561 A | 7/1987 | Doss |
| 4,754,757 A | 7/1988 | Feucht |
| 4,907,589 A | 3/1990 | Cosman |
| 4,950,267 A | 8/1990 | Ishihara et al. |
| 4,963,142 A | 10/1990 | Loertscher |
| 4,966,144 A | 10/1990 | Rochkind et al. |
| 5,061,266 A | 10/1991 | Hakky |
| 5,080,660 A | 1/1992 | Buelna |
| 5,084,043 A | 1/1992 | Hertzmann et al. |
| 5,098,431 A | 3/1992 | Rydell |
| 5,106,376 A | 4/1992 | Mononen et al. |
| 5,108,404 A | 4/1992 | Scholten et al. |
| 5,161,533 A | 11/1992 | Prass et al. |
| 5,190,546 A | 3/1993 | Jervis |
| 5,201,729 A | 4/1993 | Hertzmann et al. |
| 5,209,748 A | 5/1993 | Daikuzono |
| 5,222,953 A | 6/1993 | Dowlatshahi |
| 5,242,439 A | 9/1993 | Larsen et al. |
| 5,273,026 A | 12/1993 | Wilk |
| 5,281,213 A | 1/1994 | Milder et al. |
| 5,320,617 A | 6/1994 | Leach |
| 5,350,377 A | 9/1994 | Winston et al. |
| 5,366,443 A | 11/1994 | Eggers et al. |
| 5,368,031 A | 11/1994 | Cline et al. |
| 5,374,265 A | 12/1994 | Sand |
| 5,391,197 A | 2/1995 | Burdette et al. |
| 5,419,767 A | 5/1995 | Eggers et al. |
| 5,433,739 A | 7/1995 | Sluijter et al. |
| 5,437,661 A | 8/1995 | Rieser |
| 5,441,499 A | 8/1995 | Fritzsch |
| 5,443,463 A | 8/1995 | Stern et al. |
| 5,458,596 A | 10/1995 | Lax et al. |
| 5,458,597 A | 10/1995 | Edwards et al. |
| 5,472,441 A | 12/1995 | Edwards et al. |
| 5,484,432 A | 1/1996 | Sand |
| 5,486,170 A | 1/1996 | Winston et al. |
| 5,514,130 A | 5/1996 | Baker |
| 5,540,684 A | 7/1996 | Hassler, Jr. |
| 5,569,242 A | 10/1996 | Lax et al. |
| 5,571,147 A | 11/1996 | Sluijter et al. |
| 5,596,988 A * | 1/1997 | Markle et al. ................ 600/353 |
| 5,620,479 A | 4/1997 | Diederich |
| 5,630,426 A | 5/1997 | Shmulewitz et al. |
| 5,630,837 A | 5/1997 | Crowley |
| 5,643,319 A | 7/1997 | Green et al. |
| 5,647,871 A | 7/1997 | Levine et al. |
| 5,672,173 A | 9/1997 | Gough et al. |
| 5,681,282 A | 10/1997 | Eggers et al. |
| 5,683,366 A | 11/1997 | Eggers et al. |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,720,287 A | 2/1998 | Chapelon et al. |
| 5,725,494 A | 3/1998 | Brisken |
| 5,728,062 A | 3/1998 | Brisken |
| 5,733,315 A | 3/1998 | Burdette et al. |
| 5,735,280 A | 4/1998 | Sherman et al. |
| 5,735,811 A | 4/1998 | Brisken |
| 5,735,847 A | 4/1998 | Gough et al. |
| 5,738,680 A | 4/1998 | Mueller et al. |
| 5,743,904 A | 4/1998 | Edwards |
| 5,746,737 A | 5/1998 | Saadat |
| 5,752,969 A | 5/1998 | Cunci et al. |
| 5,762,066 A | 6/1998 | Law et al. |
| 5,762,616 A | 6/1998 | Talish |
| 5,766,153 A | 6/1998 | Eggers et al. |
| 5,776,092 A | 7/1998 | Farin et al. |
| 5,785,705 A | 7/1998 | Baker |
| 5,800,378 A | 9/1998 | Edwards et al. |
| 5,807,237 A * | 9/1998 | Tindel ........................... 600/114 |
| 5,807,392 A | 9/1998 | Eggers |
| 5,810,764 A | 9/1998 | Eggers et al. |
| 5,817,021 A | 10/1998 | Reichenberger |
| 5,843,019 A | 12/1998 | Eggers et al. |
| 5,843,021 A | 12/1998 | Edwards et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,904,681 A | 5/1999 | West, Jr. |
| 5,931,805 A | 8/1999 | Brisken |
| 5,935,123 A | 8/1999 | Edwards et al. |
| 5,941,722 A | 8/1999 | Chen |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,016,452 A | 1/2000 | Kasevich |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,030,402 A | 2/2000 | Thompson et al. |
| 6,032,674 A | 3/2000 | Eggers et al. |
| 6,033,411 A | 3/2000 | Preissman et al. |
| 6,035,238 A | 3/2000 | Ingle et al. |
| 6,045,532 A | 4/2000 | Eggers et al. |
| 6,050,995 A | 4/2000 | Durgin |
| 6,053,172 A | 4/2000 | Hovda et al. |
| 6,053,909 A | 4/2000 | Shadduck |
| 6,063,079 A | 5/2000 | Hovda et al. |
| 6,066,134 A | 5/2000 | Eggers et al. |
| 6,073,051 A | 6/2000 | Sharkey et al. |

(56) References Cited

U.S. PATENT DOCUMENTS

| | | |
|---|---|---|
| 6,086,585 A | 7/2000 | Hovda et al. |
| 6,090,105 A | 7/2000 | Zepeda et al. |
| 6,095,149 A | 8/2000 | Sharkey et al. |
| 6,099,514 A | 8/2000 | Sharkey et al. |
| 6,102,046 A | 8/2000 | Weinstein et al. |
| 6,104,957 A | 8/2000 | Alo et al. |
| 6,105,581 A | 8/2000 | Eggers et al. |
| 6,109,268 A | 8/2000 | Thapliyal et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,122,549 A | 9/2000 | Sharkey et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |
| 6,165,172 A | 12/2000 | Farley et al. |
| 6,168,593 B1 | 1/2001 | Sharkey et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,210,393 B1 | 4/2001 | Brisken |
| 6,210,402 B1 | 4/2001 | Olsen et al. |
| 6,210,415 B1 | 4/2001 | Bester |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,571 B1 | 5/2001 | Ellman et al. |
| 6,231,615 B1 | 5/2001 | Preissman |
| 6,235,020 B1 | 5/2001 | Cheng et al. |
| 6,235,024 B1 | 5/2001 | Tu |
| 6,238,391 B1 | 5/2001 | Olsen et al. |
| 6,241,665 B1 | 6/2001 | Negus et al. |
| 6,241,725 B1 | 6/2001 | Cosman |
| 6,245,064 B1 | 6/2001 | Lesh |
| 6,246,912 B1 | 6/2001 | Sluijter et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,277,112 B1 | 8/2001 | Underwood et al. |
| 6,277,122 B1 | 8/2001 | McGahan et al. |
| 6,280,441 B1 | 8/2001 | Ryan |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,426 B1 | 11/2001 | Goldberg et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,363,937 B1 | 4/2002 | Hovda et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,416,507 B1 | 7/2002 | Eggers et al. |
| 6,416,508 B1 | 7/2002 | Eggers et al. |
| 6,423,059 B1 | 7/2002 | Hanson et al. |
| 6,432,103 B1 | 8/2002 | Ellsberry et al. |
| 6,436,060 B1 | 8/2002 | Talish |
| 6,451,013 B1 | 9/2002 | Bays et al. |
| 6,454,727 B1 | 9/2002 | Burbank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,478,793 B1 | 11/2002 | Cosman et al. |
| 6,482,201 B1 | 11/2002 | Olsen et al. |
| 6,500,173 B2 | 12/2002 | Underwood et al. |
| 6,527,759 B1 | 3/2003 | Tachibana et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,560,486 B1 | 5/2003 | Osorio et al. |
| 6,575,968 B1 | 6/2003 | Eggers et al. |
| 6,582,423 B1 | 6/2003 | Thapliyal et al. |
| 6,585,656 B2 | 7/2003 | Masters |
| 6,589,237 B2 | 7/2003 | Woloszko et al. |
| 6,595,990 B1 | 7/2003 | Weinstein et al. |
| 6,602,248 B1 | 8/2003 | Sharps et al. |
| 6,622,731 B2 | 9/2003 | Daniel et al. |
| 6,632,193 B1 | 10/2003 | Davison et al. |
| 6,632,220 B1 | 10/2003 | Eggers et al. |
| 6,659,106 B1 | 12/2003 | Hovda et al. |
| 6,699,242 B2 | 3/2004 | Heggeness |
| 6,726,684 B1 | 4/2004 | Woloszko et al. |
| 6,736,835 B2 | 5/2004 | Pellegrino et al. |
| 6,746,447 B2 | 6/2004 | Davison et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,960,204 B2 | 11/2005 | Eggers et al. |
| 6,974,453 B2 | 12/2005 | Woloszko et al. |
| 7,048,743 B2 | 5/2006 | Miller et al. |
| 7,090,672 B2 | 8/2006 | Underwood et al. |
| 7,131,969 B1 | 11/2006 | Hovda et al. |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich |
| 7,217,268 B2 | 5/2007 | Eggers et al. |
| 7,258,690 B2 | 8/2007 | Sutton et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |

(56) References Cited

U.S. PATENT DOCUMENTS

| | | |
|---|---|---|
| 7,318,823 B2 | 1/2008 | Sharps et al. |
| 7,326,203 B2 | 2/2008 | Papineau et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,507,236 B2 | 3/2009 | Eggers et al. |
| 7,553,307 B2 | 6/2009 | Bleich et al. |
| 7,555,343 B2 | 6/2009 | Bleich |
| 7,645,277 B2 | 1/2010 | McClurken et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,819,826 B2 | 10/2010 | Diederich et al. |
| 7,819,869 B2 | 10/2010 | Godara et al. |
| 7,824,398 B2 | 11/2010 | Woloszko et al. |
| 7,824,404 B2 | 11/2010 | Godara et al. |
| 7,857,813 B2 | 12/2010 | Schmitz et al. |
| 7,901,403 B2 | 3/2011 | Woloszko et al. |
| 7,909,827 B2 | 3/2011 | Reiley et al. |
| 7,917,222 B1 | 3/2011 | Osorio et al. |
| 7,918,849 B2 | 4/2011 | Bleich et al. |
| 7,945,331 B2 | 5/2011 | Vilims |
| 7,963,915 B2 | 6/2011 | Bleich |
| 8,066,702 B2 | 11/2011 | Rittman, III et al. |
| 8,083,736 B2 | 12/2011 | McClurken et al. |
| 8,100,896 B2 | 1/2012 | Podhajsky |
| 8,192,424 B2 | 6/2012 | Woloszko et al. |
| 8,192,435 B2 | 6/2012 | Bleich et al. |
| 8,265,747 B2 | 9/2012 | Rittman, III et al. |
| 8,282,628 B2 | 10/2012 | Paul et al. |
| 8,292,887 B2 | 10/2012 | Woloszko et al. |
| 8,323,279 B2 | 12/2012 | Dahla et al. |
| 8,355,799 B2 | 1/2013 | Marion et al. |
| 8,361,067 B2 | 1/2013 | Pellegrino et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,507 B2 | 4/2013 | Pellegrino et al. |
| 8,535,309 B2 | 9/2013 | Pellegrino et al. |
| 8,613,744 B2 | 12/2013 | Pellegrino et al. |
| 8,623,014 B2 | 1/2014 | Pellegrino et al. |
| 8,628,528 B2 | 1/2014 | Pellegrino et al. |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0029370 A1 | 10/2001 | Hodva et al. |
| 2001/0029373 A1 | 10/2001 | Baker et al. |
| 2001/0032001 A1 | 10/2001 | Ricart et al. |
| 2001/0047167 A1 | 11/2001 | Heggeness |
| 2001/0049522 A1 | 12/2001 | Eggers et al. |
| 2001/0051802 A1 | 12/2001 | Woloszko et al. |
| 2001/0056280 A1 | 12/2001 | Underwood et al. |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0052600 A1 | 5/2002 | Davison et al. |
| 2002/0068930 A1 | 6/2002 | Tasto et al. |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0120259 A1 | 8/2002 | Lettice et al. |
| 2002/0147444 A1 | 10/2002 | Shah et al. |
| 2002/0151885 A1 | 10/2002 | Underwood et al. |
| 2002/0188284 A1 | 12/2002 | To et al. |
| 2002/0193789 A1 | 12/2002 | Underwood et al. |
| 2003/0009164 A1 | 1/2003 | Woloszko et al. |
| 2003/0014047 A1 | 1/2003 | Woloszko et al. |
| 2003/0028189 A1 | 2/2003 | Woloszko et al. |
| 2003/0040742 A1 | 2/2003 | Underwood et al. |
| 2003/0055418 A1 | 3/2003 | Tasto et al. |
| 2003/0083592 A1* | 5/2003 | Faciszewski .................. 600/564 |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0158545 A1 | 8/2003 | Hovda et al. |
| 2003/0181963 A1 | 9/2003 | Pellegrino et al. |
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2004/0006339 A1 | 1/2004 | Underwood et al. |
| 2004/0024399 A1 | 2/2004 | Sharps et al. |
| 2004/0054366 A1 | 3/2004 | Davison et al. |
| 2004/0087937 A1 | 5/2004 | Eggers et al. |
| 2004/0133124 A1 | 7/2004 | Bates et al. |
| 2004/0162559 A1 | 8/2004 | Arramon et al. |
| 2004/0193151 A1 | 9/2004 | To et al. |
| 2004/0220577 A1 | 11/2004 | Cragg et al. |
| 2004/0230190 A1 | 11/2004 | Dahla et al. |
| 2005/0004634 A1 | 1/2005 | Ricart et al. |
| 2005/0010203 A1 | 1/2005 | Edwards et al. |
| 2005/0010205 A1 | 1/2005 | Hovda et al. |
| 2005/0182417 A1 | 8/2005 | Pagano |
| 2005/0192564 A1 | 9/2005 | Cosman et al. |
| 2005/0209659 A1 | 9/2005 | Pellegrino et al. |
| 2005/0283148 A1 | 12/2005 | Janssen et al. |
| 2006/0004369 A1 | 1/2006 | Patel et al. |
| 2006/0064101 A1 | 3/2006 | Arramon |
| 2006/0095026 A1 | 5/2006 | Ricart et al. |
| 2006/0095028 A1 | 5/2006 | Bleich |
| 2006/0122458 A1 | 6/2006 | Bleich |
| 2006/0129101 A1 | 6/2006 | McGuckin |
| 2006/0178670 A1 | 8/2006 | Woloszko et al. |
| 2006/0229625 A1 | 10/2006 | Truckai et al. |
| 2006/0253117 A1 | 11/2006 | Hovda et al. |
| 2006/0264957 A1 | 11/2006 | Cragg et al. |
| 2006/0276749 A1 | 12/2006 | Selmon et al. |
| 2007/0118142 A1 | 5/2007 | Krueger et al. |
| 2007/0129715 A1 | 6/2007 | Eggers et al. |
| 2007/0149966 A1 | 6/2007 | Dahla et al. |
| 2007/0179497 A1 | 8/2007 | Eggers et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2009/0030308 A1 | 1/2009 | Bradford et al. |
| 2009/0069807 A1 | 3/2009 | Eggers et al. |
| 2009/0105775 A1 | 4/2009 | Mitchell et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0222053 A1 | 9/2009 | Gaunt et al. |
| 2009/0312764 A1 | 12/2009 | Marino |
| 2010/0016929 A1 | 1/2010 | Prochazka |
| 2010/0023006 A1 | 1/2010 | Ellman |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0185161 A1 | 7/2010 | Pellegrino et al. |
| 2010/0211076 A1 | 8/2010 | Germain et al. |

(56) References Cited

U.S. PATENT DOCUMENTS

| | | |
|---|---|---|
| 2010/0222777 A1 | 9/2010 | Sutton et al. |
| 2010/0298832 A1 | 11/2010 | Lau et al. |
| 2010/0324506 A1 | 12/2010 | Pellegrino et al. |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0196361 A1 | 8/2011 | Vilims |
| 2011/0264098 A1 | 10/2011 | Cobbs |
| 2011/0276001 A1 | 11/2011 | Schultz et al. |
| 2011/0319765 A1 | 12/2011 | Gertner et al. |
| 2012/0029420 A1 | 2/2012 | Vilims |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226273 A1 | 9/2012 | Nguyen et al. |
| 2012/0239050 A1 | 9/2012 | Linderman |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0103022 A1 | 4/2013 | Sutton et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2014/0039500 A1 | 2/2014 | Pellegrino et al. |
| 2014/0316405 A1 | 10/2014 | Pellegrino et al. |

FOREIGN PATENT DOCUMENTS

| | | |
|---|---|---|
| EP | 0597463 | 5/1994 |
| EP | 1013228 | 6/2000 |
| EP | 1059067 | 12/2000 |
| EP | 1059087 | 12/2000 |
| JP | 60-016764 | 2/1985 |
| JP | 6-47058 | 2/1994 |
| JP | 10-290806 | 11/1998 |
| JP | 2001-037760 | 2/2001 |
| JP | 2005-169012 | 6/2005 |
| WO | WO 96/36289 | 11/1996 |
| WO | WO 98/27876 | 7/1998 |
| WO | WO 98/34550 | 8/1998 |
| WO | WO 99/19025 | 4/1999 |
| WO | WO 99/44519 | 9/1999 |
| WO | WO 99/48621 | 9/1999 |
| WO | WO 00/21448 | 4/2000 |
| WO | WO 00/33909 | 6/2000 |
| WO | WO 00/49978 | 8/2000 |
| WO | WO 00/56237 | 9/2000 |
| WO | WO 00/67656 | 11/2000 |
| WO | WO 00/67848 | 11/2000 |
| WO | WO 01/01877 | 1/2001 |
| WO | WO 01/45579 | 6/2001 |
| WO | WO 01/57655 | 8/2001 |
| WO | WO 02/05699 | 1/2002 |
| WO | WO 02/05897 | 1/2002 |
| WO | WO 02/28302 | 4/2002 |
| WO | WO 02/054941 | 7/2002 |
| WO | WO 02/067797 | 9/2002 |
| WO | WO 02/096304 | 12/2002 |
| WO | WO 2007/031264 | 3/2007 |
| WO | WO 2008/001385 | 1/2008 |
| WO | WO 2008/008522 | 1/2008 |
| WO | WO 2008/121259 | 10/2008 |

OTHER PUBLICATIONS

Antonacci, M. Darryl et al.; Innervation of the Human Vertebral Body: A Histologic Study; Journal of Spinal Disorder, vol. 11, No. 6, pp. 526-531, 1998 Lippincott Williams & Wilkins, Philadelphia.

Arnoldi, Carl C.; Intraosseous Hypertension—A Possible Cause of Low Back Pain?; Clinical Orthopedics and Related Research, No. 115, Mar.-Apr. 1976.

Bergeron et al., "Fluoroscopic-guided radiofrequency ablation of the basivertebral nerve: application and analysis with multiple imaging modalities in an ovine model," Thermal Treatment of Tissue: Energy Delivery and Assessment III, edited by Thomas P. Ryan, Proceedings of SPIE, vol. 5698 (SPIE, Bellingham, WA, 2005) pp. 156-167.

Bogduk, Nikolai, et al.; Technical Limitations to the efficacy of Radiofrequency Neurotomy for Spinal Pain; Neurosurgery vol. 20, No. 4, 1987.

Choy, Daniel SS.J. et al.; Percutaneous Laser Disc Decompression, A New Therapeutic Modality; SPINE vol. 17, No. 8, 1992.

Cosman, E.R. et al., Theoretical Aspects of Radiofrequency Lesions in the Dorsal Root Entry Zone. Neurosurgery, vol. 1, No. 6, 1984, pp. 945-950.

Deardorff, Dana L. et al.; Ultrasound applicators with internal cooling for interstitial thermal therapy; SPIE vol. 3594, 1999.

Dupuy, D.E. et al. Radiofrequency ablation of spinal tumors: Temperature distribution in the spinal canal AJR, vol. 175, pp. 1263-1266, Nov. 2000.

Dupuy, Damian E.; Radiofrequency Ablation: An Outpatient Percutaneous Treatment; Medicine and Health/Rhode Island vol. 82, No. 6, Jun. 1999.

Deramond, H. et al., Temperature Elevation Caused by Bone Cement Polymerization During Vertebroplasty, Bone, Aug. 1999, pp. 17S-21S, vol. 25, No. 2, Supplement.

Diederich, C. J. et al., "IDTT Therapy in Cadaveric Lumbar Spine: Temperature and thermal dose distributions, Thermal Treatment of Tissue: Energy Delivery and Assessment," Thomas P. Ryan, Editor, Proceedings of SPIE vol. 4247:104-108 (2001).

Diederich, Chris J. et al.; Ultrasound Catheters for Circumferential Cardiac Ablation; SPIE vol. 3594 (1999).

Esses, Stephen I. et al.; Intraosseous Vertebral Body Pressures; SPINE vol. 17 No. 6 Supplement 1992.

FDA Response to 510(k) Submission by Relievant Medsystems, Inc. submitted on Sep. 27, 2007 (date stamped on Oct. 5, 2007) and associated documents.

Goldberg, S.N. et al., Tissue ablation with radiofrequency: Effect of probe size, gauge, duration, and temperature on lesion volume, Acad. Radiol., vol. 2, pp. 399-404 (1995).

Hanai, Kenji et al.; Simultaneous Measurement of Intraosseous and Cerebrospinal Fluid Pressures in the Lumbar Region; SPINE vol. 10, No. 1, 1985.

Heggeness, Michael H. et al., The Trabecular Anatomy of Thoracolumbar Vertebrae: Implications for Burst Fractures, Journal of Anatomy, 1997, pp. 309-312, vol. 191, Great Britain.

Heggeness, Michael H. et al. Discography Causes End Plate Deflection; SPINE vol. 18, No. 8, pp. 1050-1053, 1993, J.B. Lippincott Company.

Hoopes et al., "Radiofrequency Ablation of the Basivertebral Nerve as a Potential Treatment of Back Pain: Pathologic Assessment in an Ovine Model," Thermal Treatment of Tissue: Energy Delivery and Assessment III, edited by Thomas P. Ryan, Proceedings of SPIE, vol. 5698 (SPIE, Bellingham, WA, 2005) pp. 168-180.

Houpt, Jonathan C. et al.; Experimental Study of Temperature Distributions and Thermal Transport During Radiofrequency Current Therapy of the Intervertebral Disc; SPINE vol. 21, No. 15, pp. 1808-1813, 1996, Lippincott-Raven Publishers.

Kleinstueck, Frank S. et al.; Acute Biomechanical and Histological Effects of Intradiscal Electrothermal Therapy on Human Lumbar Discs; SPINE vol. 26, No. 20, pp. 2198-2207; 2001, Lippincott Williams & Wilkins, Inc.

Kopecky, Kenyon K. et al. "Side-Exiting Coaxial Needle for Aspiration Biopsy"—AJR—1996; 167, pp. 661-662.

Lehmann, Justus F. et al.; Selective Heating Effects of Ultrasound in Human Beings; Archives of Physical Medicine & Rehabilitation Jun. 1966.

Letcher, Frank S. et al.; The Effect of Radiofrequency Current and Heat on Peripheral Nerve Action Potential in the Cat; U.S. Naval Hospital, Philadelphia, PA (1968).

Lundskog, Jan; Heat and Bone Tissue-/an experimental investigation of the thermal properties of bone tissue and threshold levels for

(56) References Cited

OTHER PUBLICATIONS thermal injury; Scandinavian Journal of Plastic and Reconstructive Surgery Supplemental 9, From the Laboratory of Experimental Biology, Department of anatomy, University of Gothenburg, Gothenburg, Sweden, Goteborg 1972.

Martin, J.B. et al., Vertebroplasty: Clinical Experience and Follow-up Results, Bone, Aug. 1999, pp. 11S-15S, vol. 25, No. 2, Supplement.

Massad, Malek M.D. et al.; Endoscopic Thoracic Sympathectomy: Evaluation of Pulsatile Laser, Non-Pulsatile Laser, and Radiofrequency-Generated thermocoagulation; Lasers in Surgery and Medicine; 1991; pp. 18-25.

Mehta, Mark et al.; The treatment of chronic back pain; Anaesthesia, 1979, vol. 34, pp. 768-775.

Nau, William H., Ultrasound interstitial thermal therapy (USITT) in the prostate; SPIE vol. 3594, Jan. 1999.

Rashbaum, Ralph F.; Radiofrequency Facet Denervation: A Treatment alternative in Refractory Low Back Pain with or without Leg Pain; Orthopedic Clinics of North America, vol. 14, No. 3, Jul. 1983.

Rosenthal, D.I., Seminars in Musculoskeletal Radiology, vol. 1, No. 2., pp. 265-272 (1997).

Ryan et al., "Three-Dimensional Finite Element Simulations of Vertebral Body Thermal Treatment," Thermal Treatment of Tissue: Energy Delivery and Assessment III, edited by Thomas P. Ryan, Proceedings of SPIE, vol. 5698 (SPIE, Bellingham, WA, 2005) pp. 137-155.

Shealy, C. Norman; Percutaneous radiofrequency denervation of spinal facets: Treatment for chronic back pain and sciatica; Journal of Neurosurgery/vol. 43/Oct. 1975.

Sherman, Mary S.; The Nerves of Bone, The Journal of Bone and Joint Surgery, Apr. 1963, pp. 522-528, vol. 45-A, No. 3.

Solbiati, L. et al. Hepatic metastases: Percutaneous radio-frequency ablation with cooled-tip electrodes. Interventional Radiology, vol. 205, No. 2, pp. 367-373 (1997).

Stanton, Terry, "Can Nerve Ablation Reduce Chronic Back Pain?" AAOS Now, Jan. 2012.

The AVAmax System—Cardinal Health Special Procedures, Lit. No. 25P0459-01-www.cardinal.com (copyright 2007).

Tillotson, L. et al. Controlled thermal injury of bone: Report of a percutaneous technique using radiofrequency electrode and generator. Investigative Radiology, Nov. 1989, pp. 888-892.

Troussier, B. et al.; Percutaneous Intradiscal Radio-Frequency Thermocoagulation A Cadaveric Study; SPINE vol. 20, No. 15, pp. 1713-1718, 1995, Lippincott-Raven Publishers.

* cited by examiner

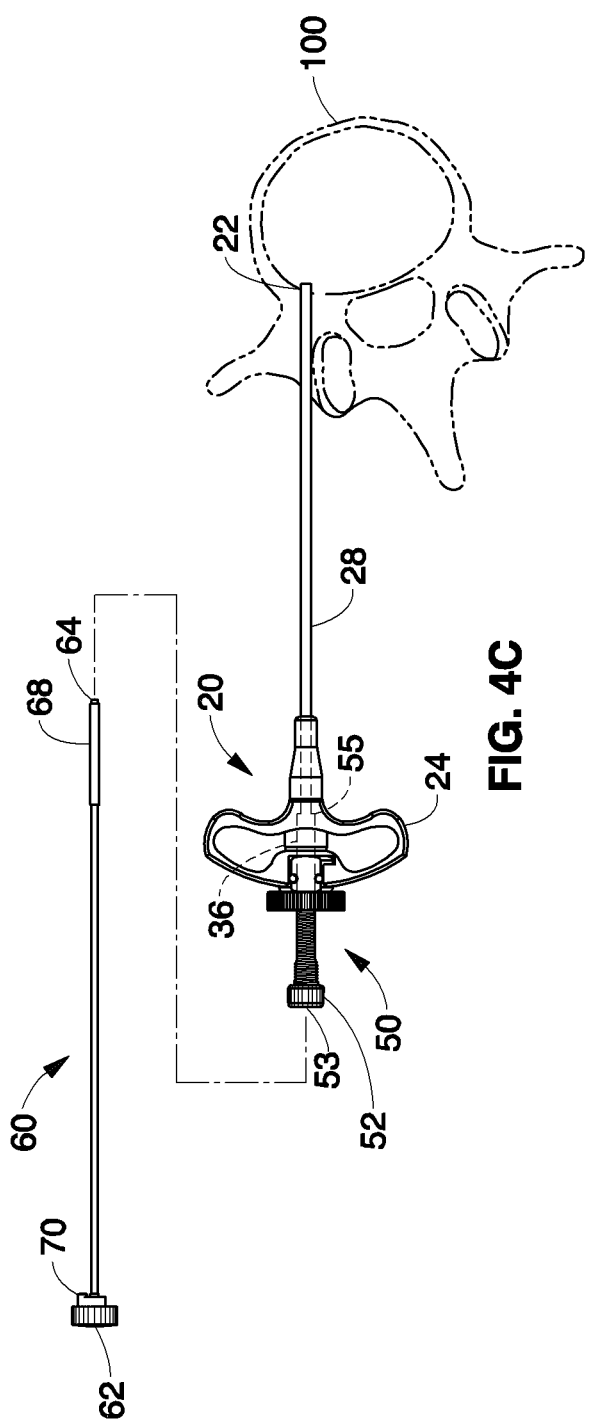
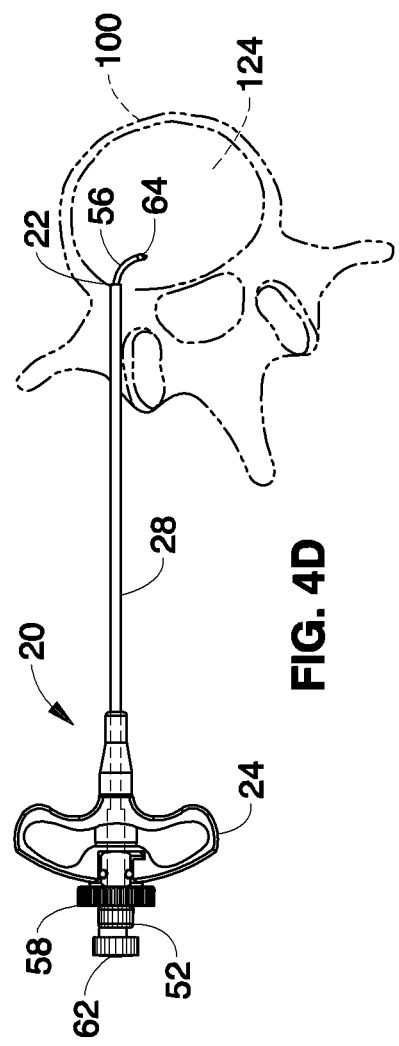
FIG. 4C
FIG. 4D

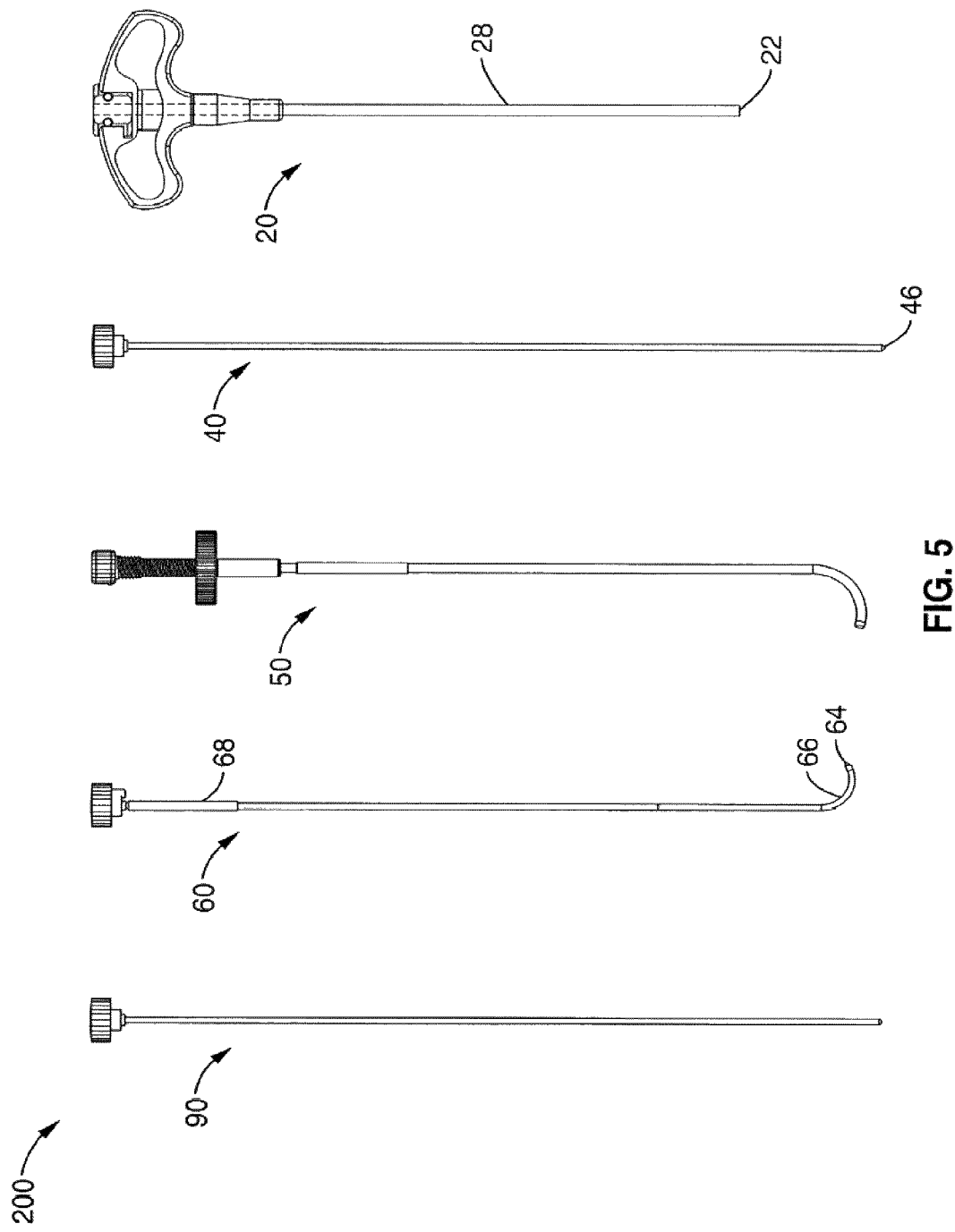

CHANNELING PATHS INTO BONE

CROSS-REFERENCE TO RELATED APPLICATIONS

This application is a continuation of U.S. patent application Ser. No. 13/862,242, filed on Apr. 12, 2013, which is a divisional of U.S. patent application Ser. No. 12/566,895 filed on Sep. 25, 2009, which claims the benefit of U.S. Provisional Application 61/100,553 filed on Sep. 26, 2008, each of which is expressly incorporated in its entirety by reference herein.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to generating passageways through tissue, and more particularly to creating curved paths in bone.

2. Description of Related Art

Recently, the technique of accessing the vertebral body through minimally invasive means has been developed through the surgical techniques used in vertebroplasty and kyphoplasty. Although accessing the vertebral segments of the spine through the pedicle and into the lateral/anterior section of the body of the vertebra is the primary method of placing a treatment device (e.g. a bone cement delivery device and/or an RF probe) into the vertebra, it is difficult to place a probe in the posterior midline section of the vertebra. Furthermore, accessing the posterior midline section of the S1 segment of the spine is difficult with a straight linear access route. A probe preferably needs to be capable of navigating to the posterior section of the S1 vertebral body as well as the same target area within a lumbar vertebral segment. In addition, it is contemplated that spinal segments in the cervical and thoracic spine may also be targeted.

In order to accurately and predictably place a treatment device in the posterior midline section of a lumbar vertebral body or S1 vertebral body, the device or probe needs to navigate to said area through varying densities of bone. However due to the varying densities of bone, it is difficult to navigate a probe in bone and ensure its positioning will be in the posterior midline section of the vertebral body.

Current techniques for tissue aspirations require a coaxial needle system that allows taking several aspirates through a guide needle without repositioning the guide needle. However the problem with this system is that after the first pass of the inner needle in to the lesion, subsequent passes tend of follow the same path within the mass, yielding only blood not diagnostic cells.

A scientific paper written by Kopecky et al., entitled "Side-Exiting Coaxial Needle for Aspiration Biopsy," describes the use of a side exiting coaxial needle to allow for several aspiration biopsies. The guide needle has a side hole 1 cm from the distal tip. When a smaller needle is advanced through this new guide needle, the smaller needle is deflected by a ramp inside the guide, causing the smaller needle to exit through the side hole. Although this side exiting needle is able to deflect a bone aspiration needle, it does not guarantee that the needle exits the side hole in a linear direction into the tissue site. Once the tissue aspiration needle exits the needle, it will deviate from a linear path depending on the density of the tissue and inherent material strength of the needle. This is an inherent problem the device is unable to overcome.

Accordingly, an object of the present invention is a system and method for generating a path in bone that predictably follows a predetermined curved path.

BRIEF SUMMARY OF THE INVENTION

The present invention is directed to systems and methods to deploy and navigate a flexible treatment instrument, such as an RF bipolar probe, within bone. Although the systems and methods described below are primarily directed to navigating bone through a vertebral member of the spine, and particularly to treat the BVN of a vertebral member, it is appreciated that the novel aspects of the present invention may be applied to any tissue segment of the body.

The first novel principle of this invention is the ability to navigate a curve or angle within varying densities of cancellous bone and create a straight channel at the end of the navigated curve or angle. Several systems are described.

One aspect is a method of therapeutically treating a vertebral body having an outer cortical bone region and an inner cancellous bone region, and a BVN having a trunk extending from the outer cortical bone region into the inner cancellous region and a branches extending from the trunk to define a BVN junction, comprising the steps of: a) inserting an energy device into the vertebral body, and b) exclusively depositing energy within the inner cancellous bone region of the vertebral body between, but exclusive of the BVN junction and the outer cortical bone region, to denervate the BVN.

In another aspect of the present invention, a tube-within-tube embodiment has a deployable curved Nitinol tube that deploys from a straight cannula. The Nitinol tube is pre-curved to create an angular range of approximately 0° to approximately 180°, but more specifically from approximately 45° to approximately 110°, when fully deployed from the straight cannula. The design of the curve is such that the flexible element (carrying the treatment device) can navigate through the angular range of deployment of the nitinol tube. The curved nitinol tube allows the flexible element to navigate through a curve within bone without veering off towards an unintended direction. Cancellous bone density varies from person to person. Therefore, creating a curved channel within varying density cancellous bone will generally not predictably or accurately support and contain the treatment device as it tries to navigate the curved channel. With the present invention, the flexible element is deployed into the bone through the curved Nitinol tube, which supports the element as it traverses through the curve. When it departs from the tube, it will do so in a linear direction towards the target zone. This design allows the user to predictably and accurately deploy the flexible element towards the target zone regardless of the density of the cancellous bone.

An aspect of the invention is a system for channeling a path into bone. The system comprises a trocar having a central channel and opening at its distal tip, and a cannula sized to be received in said central channel and delivered to said distal opening. The cannula has a deflectable tip with a preformed curve such that the tip straightens while being delivered through the trocar and regains its preformed curve upon exiting and extending past the distal opening of the trocar to generate a curved path in the bone corresponding to the preformed curve of the deflectable tip. The cannula comprises a central passageway having a diameter configured allow a treatment device to be delivered through the central passageway to a location beyond the curved path.

In one embodiment, the system further includes a straight stylet configured to be installed in the trocar, wherein the straight stylet comprises a sharp distal tip that is configured to extend beyond the distal opening of the trocar to pierce the bone as the trocar is being delivered to a treatment location within the bone.

The system may further include a straightening stylet configured to be installed in the cannula, wherein the straightening stylet comprising a rigid construction configured to straighten the distal tip of the cannula when positioned in the trocar.

In an alternative embodiment, the straightening stylet further comprises a sharp distal end to pierce the bone, and the straightening stylet and cannula are installed in the trocar in place of the straight stylet as the trocar is delivered into the bone.

In a preferred embodiment, the system further includes a curved stylet having an outer radius sized to fit within the central passageway of the curved cannula. The curved stylet is configured to be installed in the curved cannula while the curved cannula is extended past the distal opening of the trocar, the curved stylet configured to block the distal opening of the curved cannula while being delivered into the bone. Preferably, the curved stylet has a curved distal end corresponding to the curve of the curved cannula.

The curved stylet also has a sharp distal tip configured to extend past the curved cannula to pierce the bone as the cannula is delivered past the distal opening of the trocar. The curved stylet also preferably comprises an angled distal tip configured to further support and maintain the curved stylet radius as it is delivered past the distal opening of the trocar and into bone.

Preferably, the curved stylet and the curved cannula have mating proximal ends that align the curve of the curved stylet with the curve of the curved cannula.

In one embodiment, the system further includes a straight channeling stylet configured to be installed in the cannula after removing the curved stylet, wherein the straight channeling stylet is flexibly deformable to navigate the curved cannula yet retain a straight form upon exiting the curve cannula, and wherein straight channeling stylet has a length longer than the curved cannula such that it creates a linear path beyond the distal end of the curved cannula when fully extended.

Another aspect is method for channeling a path into bone to a treatment location in the body of a patient. The method includes the steps of inserting a trocar having a central channel and opening at its distal tip into a region of bone at or near the treatment location, and delivering a cannula through said central channel and to said distal opening, wherein the cannula comprises a deflectable tip with a preformed curve such that the tip straightens while being delivered through the trocar and regains its preformed curve upon exiting the trocar, and extending the cannula past the distal opening of the trocar to generate a curved path in the bone corresponding to the preformed curve of the deflectable tip. Finally, a treatment device is delivered through a central passageway in said cannula to the treatment location beyond the curved path.

In one embodiment, inserting a trocar into a region of bone comprises inserting a stylet into the trocar such that the stylet extends beyond the distal opening of the trocar, and inserting the stylet and trocar simultaneously into the region of bone such that the stylet pierces the bone as the trocar is being delivered to a treatment location.

In another embodiment, delivering a cannula through the central channel comprises inserting a straightening stylet into the central passageway of the cannula, wherein the straightening stylet comprises a rigid construction configured to straighten the curved distal tip of the cannula, and inserting the straightening stylet and straightened cannula simultaneously into the trocar.

In an alternative embodiment, the straightening stylet further comprises a sharp distal end to pierce the bone, wherein the straightening stylet and cannula are installed simultaneously along with the trocar as the trocar is delivered into the bone.

In yet another embodiment, extending the cannula past the distal opening is done by inserting a curved stylet into the central passageway of the curved cannula such that a distal tip of the curved stylet extends to at least the distal opening of the curved cannula, and simultaneously extending the curved cannula and curved stylet from the distal end of the trocar such that the curved stylet blocks the distal opening of the curved cannula while being delivered into the bone.

In a preferred embodiment, the curved stylet has a curved distal end corresponding to the curve of the curved cannula, and wherein the curved stylet reinforces the curved shape of the curved cannula as the curved cannula is extended past the distal opening of the trocar. The curved stylet has a sharp distal tip such that it is advanced within the central passageway so that the curved stylet extends past the distal opening of the curved cannula such that the curved stylet pierces the bone as the cannula is delivered past the distal opening of the trocar.

In a further step, the curved stylet is removed from the curved cannula, and a straight channeling stylet is inserted into the curved distal end of the cannula. The straight channeling stylet is flexibly deformable to navigate the curved cannula, yet retain a straight form upon exiting the curved cannula. The straight channeling stylet is longer than the curved cannula to create a linear channel beyond the distal tip of the curved cannula.

In a preferred embodiment, the trocar is inserted through a cortical bone region and into a cancellous bone region of a vertebrae, and the curved cannula is extended though at least a portion of the cancellous bone region to a location at or near the treatment location. A preferred treatment location comprises a BVN of the vertebrae, and treatment is delivered to the treatment location to denervate at least a portion of the BVN. In one embodiment, a portion of the BVN is denervated by delivering focused, therapeutic heating to an isolated region of the BVN. In another embodiment, a portion of the BVN comprises is denervated delivering an agent to the treatment region to isolate treatment to that region. Preferably, the treatment is focused on a location of the BVN that is downstream of one or more branches of the BVN.

Another aspect is a kit for channeling a path into bone. The kit includes a trocar having a central channel and opening at its distal tip, and a cannula selected from a set of cannulas sized to be received in said central channel and delivered to said distal opening. The cannula has a deflectable distal tip with a preformed curve such that the tip straightens while being delivered through the trocar and regains its preformed curve upon exiting and extending past the distal opening of the trocar to generate a curved path in the bone corresponding to the preformed curve of the deflectable tip. The cannula comprises a central passageway having a diameter configured allow a treatment device to be delivered through the central passageway to a location beyond the curved path, wherein the set of cannulas comprises one or more cannulas that have varying preformed curvatures at the distal tip.

In a preferred embodiment, the one or more cannulas have a varying preformed radius at the distal tip. In addition, the one or more cannulas each have distal tips that terminate at varying angles with respect to the central channel of the trocar. The length of the distal tips may also be varied. The angle of the distal with respect to the central channel of the trocar may vary from 0 degrees to 180 degrees.

The kit may further include a straight stylet configured to be installed in the trocar, the straight stylet comprising a sharp distal tip that is configured to extend beyond the distal opening of the trocar to pierce the bone as the trocar is being delivered to a treatment location within the bone.

In a preferred embodiment, the kit includes a set of curved stylets having an outer radius sized to fit within the central passageway of the curved cannula, wherein each curved stylet is configured to be installed in the curved cannula while the curved cannula is extended past the distal opening of the trocar. The curved stylet is configured to block the distal opening of the curved cannula while being delivered into the bone. Each curved stylet has a varying curved distal end corresponding to the curve of a matching curved cannula in the set of curved cannulas. The curved stylet has a sharp distal tip configured to extend past the curved cannula to pierce the bone as the cannula is delivered past the distal opening of the trocar.

In another embodiment, the kit includes a set of straight channeling stylets wherein one of the set of stylets is configured to be installed in the cannula after removing the curved stylet. The straight channeling stylet is flexibly deformable to navigate the curved cannula yet retain a straight form upon exiting the curve cannula. Each of the straight channeling stylets has a varying length longer than the curved cannula such that the straight channeling stylet creates a predetermined-length linear path beyond the distal end of the curved cannula when fully extended.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIGS. 4A-F illustrate a method for accessing the BVN with the system of the present invention.

FIG. 5 shows an alternative system for generating a curved path in bone according to the present invention.

Figure 6:
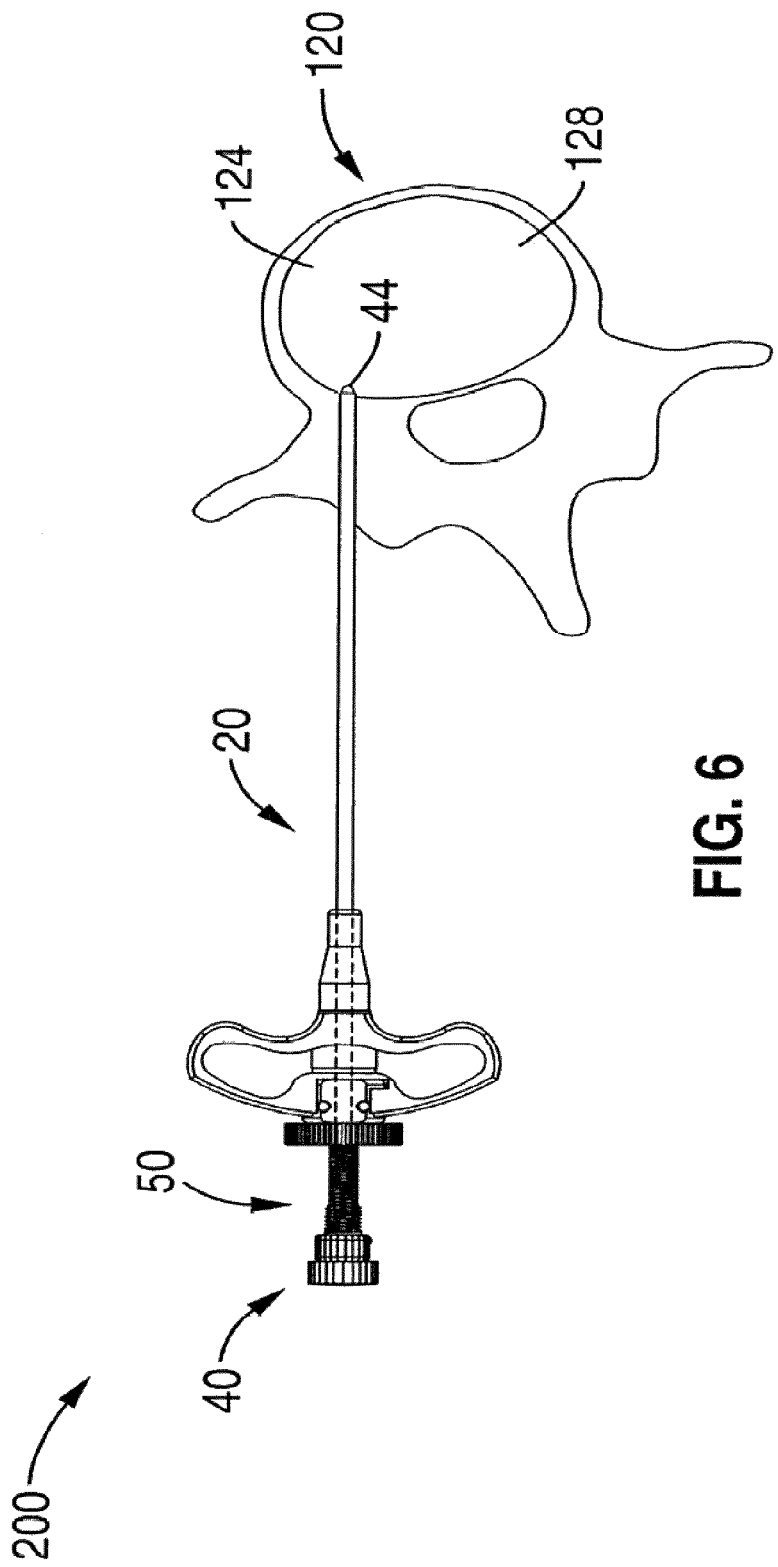

FIG. 6 shows the system of FIG. 5 being installed in a vertebral body.

Figure 7B:
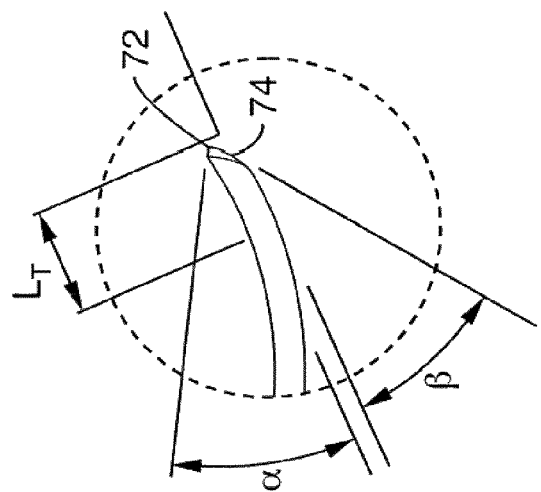
Figure 7A:
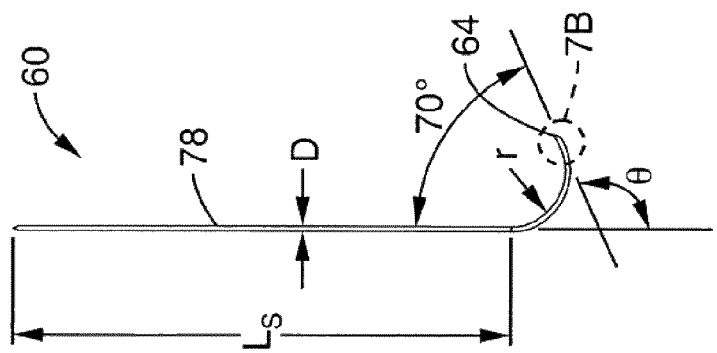

FIGS. 7A-7B show a curved stylet in accordance with the present invention.

DETAILED DESCRIPTION OF THE INVENTION

Referring more specifically to the drawings, for illustrative purposes the present invention is embodied in the apparatus generally shown in FIG. 1 through FIG. 7B. It will be appreciated that the apparatus may vary as to configuration and as to details of the parts, and that the method may vary as to the specific steps and sequence, without departing from the basic concepts as disclosed herein.

Figure 1:
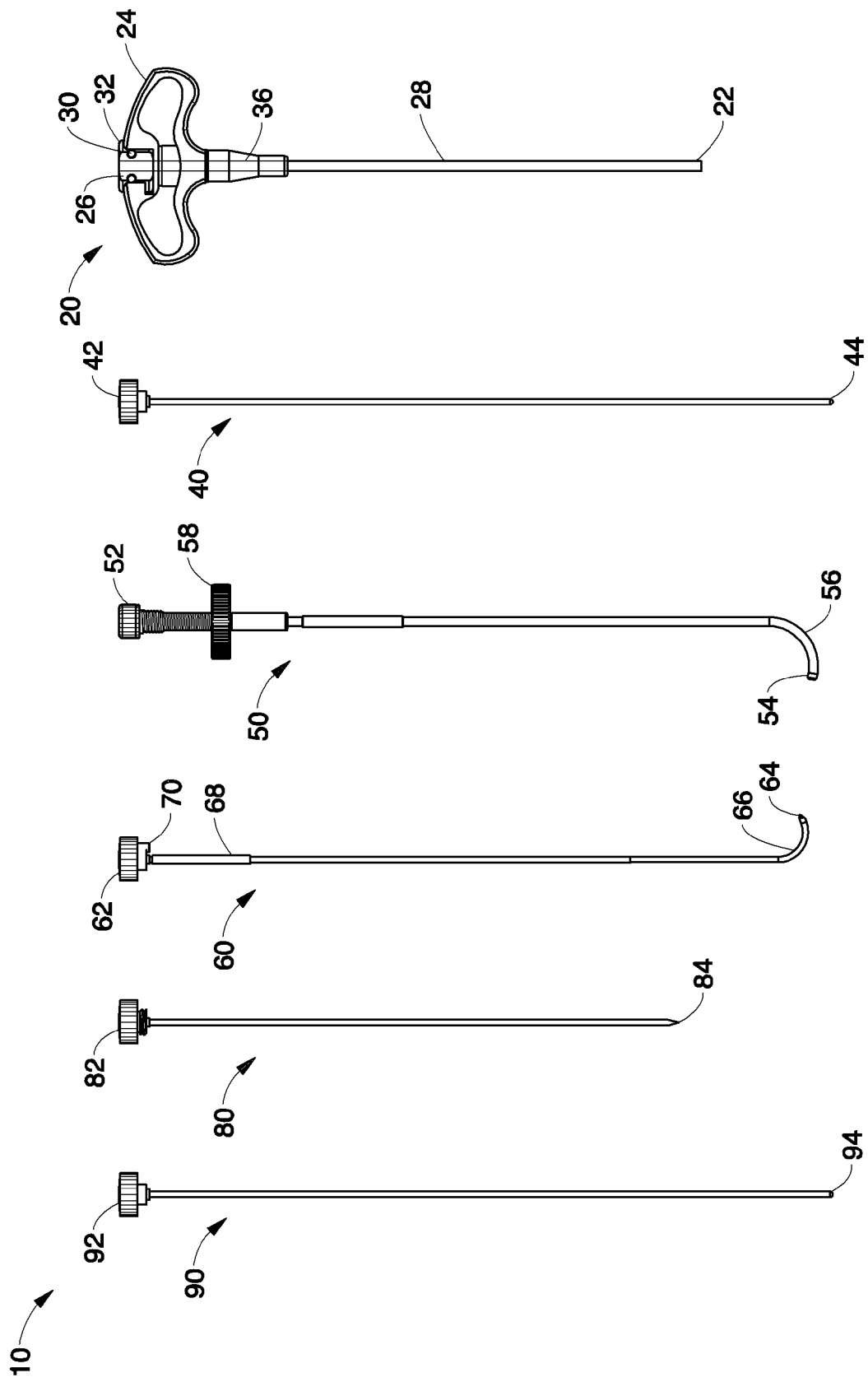
FIG. 1 is a system for generating a curved path in bone according to the present invention.
Figure 2:
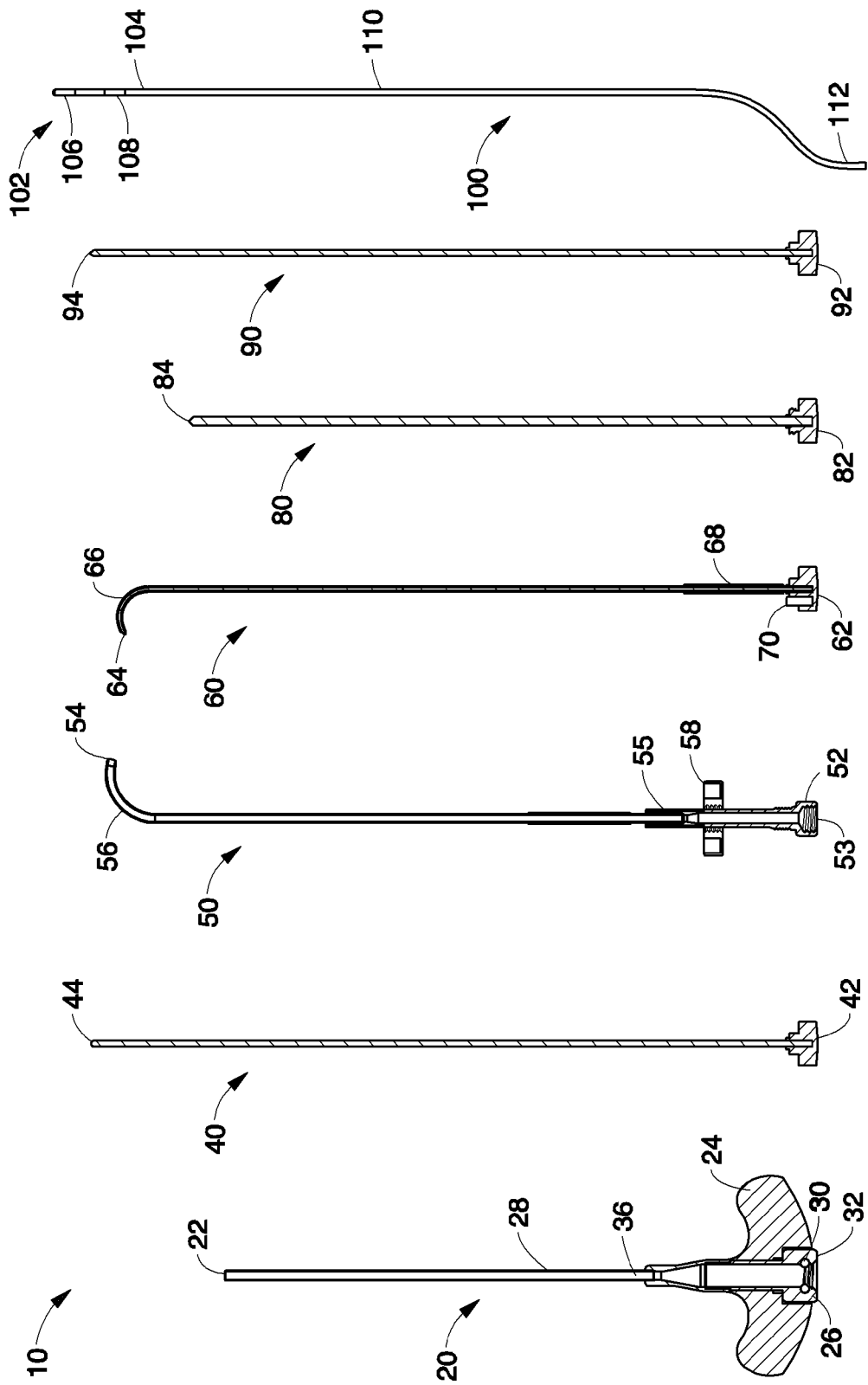
FIG. 2 is a sectional view of the system of FIG. 1

FIGS. 1 and 2 illustrate a first embodiment of the present invention comprising a system or kit 10 for forming a path through bone. The system comprises a needle trocar 20 (the main body of the instrument set). The trocar 20 comprises an elongate shaft 28 having a handle 24 at its proximal end 32 and a central lumen 36 passing through to the distal end 22 of the trocar 20. The central lumen 36 is generally sized to allow the other instruments in the system 10 to be slideably introduced into the patient to a treatment region. System 10 further comprises a straight stylet 80 having a sharp-tipped needle 84 at its distal end that is used with the needle trocar 20 to create the initial path through the soft tissue and cortical shell to allow access to the cancellous bone, a curved cannula 50 that is used to create/maintain the curved path within the bone/tissue. A straightening stylet 40 is used to straighten out the curve and load the curved cannula 50 into the needle trocar 20. A curved stylet 60 is used in conjunction with the curved cannula 50 to create the curved path within the bone/tissue, and a channeling stylet 90 is used to create a working channel for a treatment device (such as RF probe 100) beyond the end of the curved path created by the curved cannula 50.

The surgical devices and surgical systems described may be used to deliver numerous types of treatment devices to varying regions of the body. Although the devices and systems of the present invention are particularly useful in navigating through bone, it is appreciated that they may also be used to navigate through soft tissue, or through channels or lumens in the body, particularly where one lumen may branch from another lumen.

The following examples illustrate the system 10 applied to generating a curve bone path in the vertebral body, and more particularly for creating a bone path via a transpedicular approach to access targeted regions in the spine. In particular, the system 10 may be used to deliver a treatment device to treat or ablate intraosseous nerves, and in particular that basivertebral nerve (BVN). Although the system and methods provide significant benefit in accessing the BVN, it is appreciated that the system 10 of the present invention may similarly be used to create a bone path in any part of the body.

Figure 3:
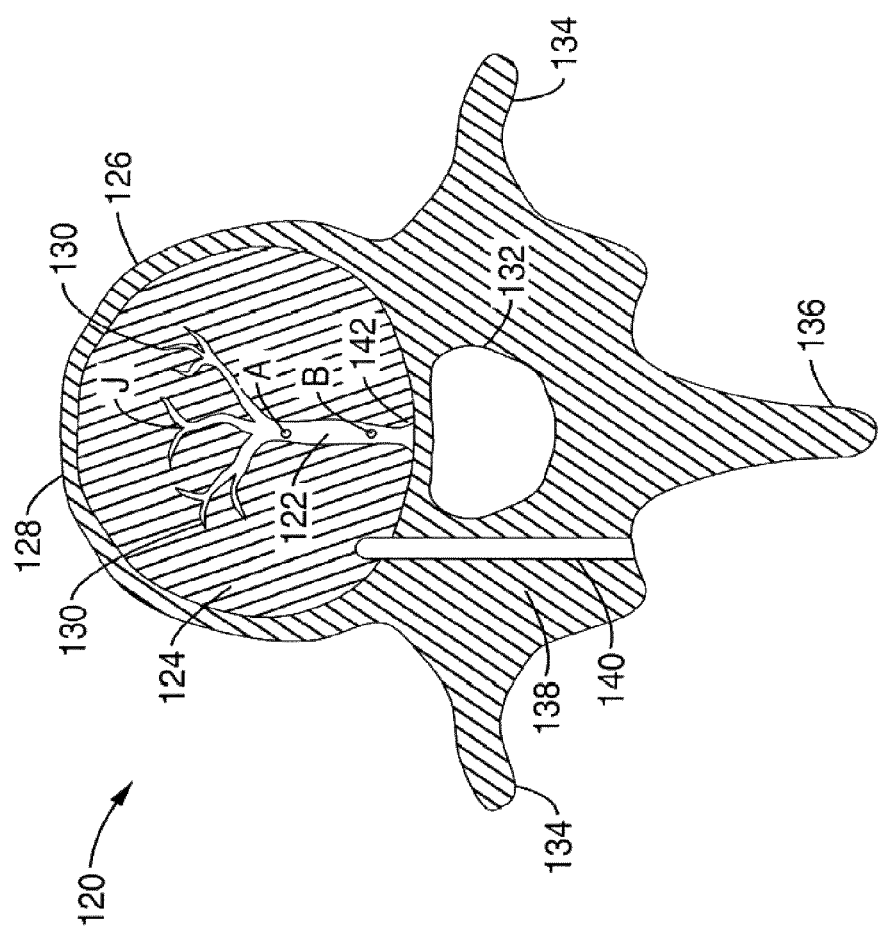
FIG. 3 illustrates a sectioned view of a vertebral body with a path bored through the cortical shell.

FIG. 3 illustrates a cross-sectional view of a vertebra 120. Recently, the existence of substantial intraosseous nerves 122 and nerve branches 130 within human vertebral bodies ("basivertebral nerves") have been identified. The basivertebral nerve 122 has at least one exit 142 point at a location along the nerve 122 where the nerve 122 exits the vertebral body 126 into the vertebral foramen 132.

Preferably, the basivertebral nerves are at, or in close proximity to, the exit point 142. Thus, the target region of the BVN 122 is located within the cancellous portion 124 of the bone (i.e., to the interior of the outer cortical bone region 128), and proximal to the junction J of the BVN 122 having a plurality of branches 130 (e.g. between points A and B along nerve 122). Treatment in this region is advantageous because only a single portion of the BVN 122 need be effectively treated to denervate or affect the entire system. Typically, treatment in accordance with this embodiment can be effectuated by focusing in the region of the vertebral body located between 60% (point A) and 90% (point B) of the distance between the anterior and posterior ends of the vertebral body. In contrast, treatment of the BVN 122 in locations more downstream than the junction J require the denervation of each branch 130.

In one approach for accessing the BVN, the patient's skin is penetrated with a surgical instrument which is then used to access the desired basivertebral nerves, i.e., percutaneously. In one embodiment, a transpedicular approach is used for penetrating the vertebral cortex to access the BVN 122. A passageway 140 is created between the transverse process 134 and spinous process 136 through the pedicle 138 into the cancellous bone region 124 of the vertebral body 126 to access a region at or near the base of the nerve 122. It is appreciated that a postereolateral approach (not shown) may also be used for accessing the nerve.

FIGS. 4A-F illustrate a preferred method for accessing the BVN with the system 10 of the present invention. First, the straight stylet 80 is inserted in aperture 26 at the proximal end 32 of needle trocar 20. The straight stylet 80 is advanced down the central lumen 36 (see FIG. 2) of the trocar 20 until the proximal stop 82 abuts against handle 24 of the trocar 20, at which point the distal tip 84 of straight stylet protrudes out of the distal end 22 of the trocar 20. The tip 84 of the straight stylet 80 preferably comprises a sharp tip for piercing soft tissue and bone.

Figure 4A:
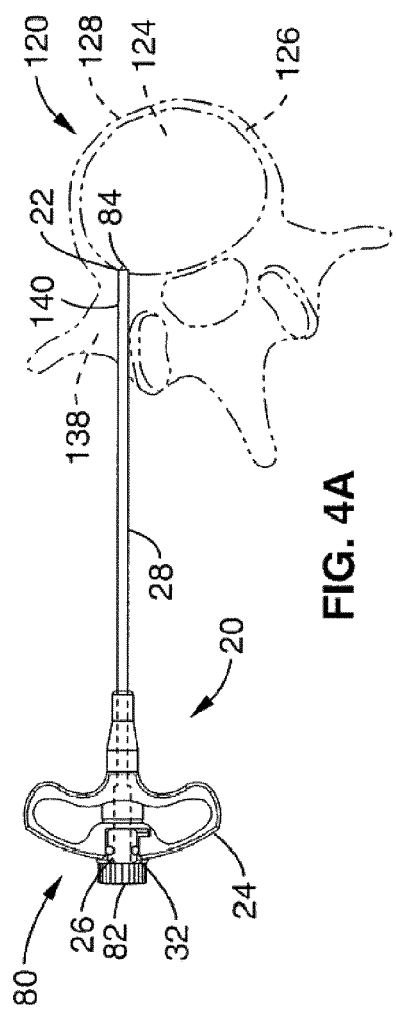

Referring now to FIG. 4A, the assembly (trocar 20 and straight stylus 80) is advanced through soft tissue to the surface of the bone. Once the proper alignment is determined, the assembly is advanced through the cortical shell of pedicle 138 and into the cancellous interior 124 of the bone.

After the proper depth is achieved, the straight stylet 80 is removed from the trocar 20, while the trocar 20 remains stationary within the vertebrae 120. The straightening stylet 40 is inserted into proximal aperture 53 (see FIG. 2) of the curved cannula 50 and advanced along the central lumen of the curved cannula 50 until the stop 42 of the stylet 40 abuts up to the proximal end 52 of the curved cannula. This forces the distal tip of the straight stylet through the curved section 56 of the curved cannula 50 to straighten out the curved section 56. It is contemplated that the straight stylet comprise a hard, non-compliant material and the distal end of the curved cannula 50 a compliant, yet memory retaining material (e.g. Nitinol, formed PEEK, etc.) such that the curved section 56 yields to the rigidity of the straightening stylet 40 when installed, yet retains its original curved shape when the stylet 40 is removed.

Figure 4B:
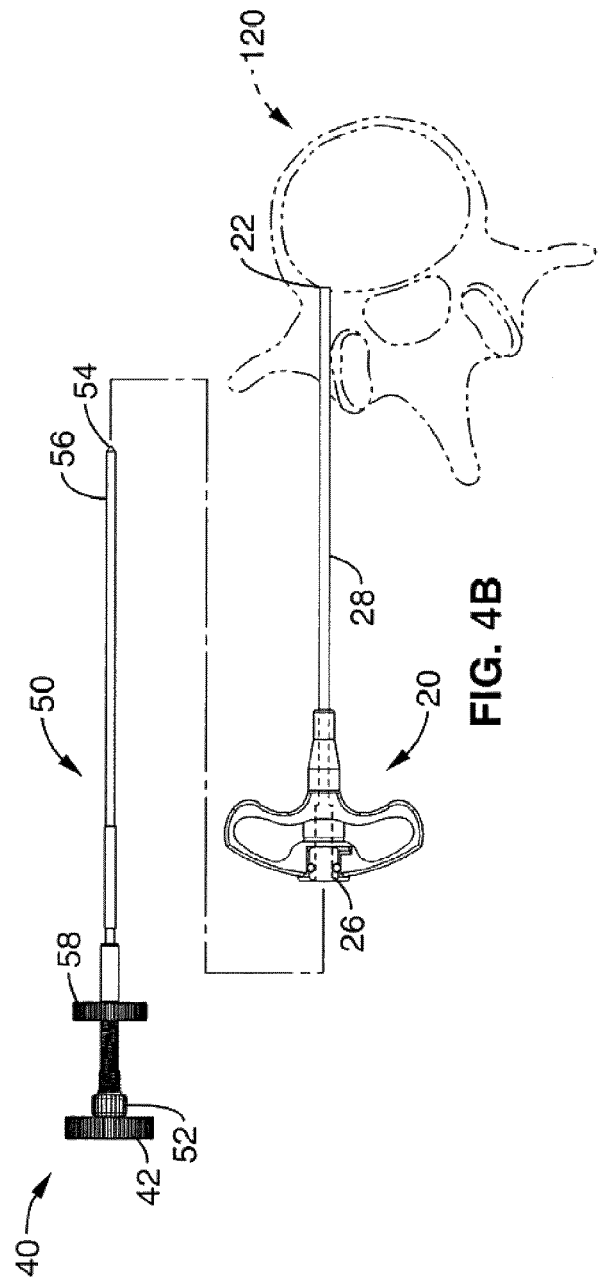

As shown in FIG. 4B, once the straightening stylet 40 is secure and the curved cannula 50 is straight, they are inserted into the needle trocar 20 and secured. Proper alignment (e.g. prevent rotation, orient curve direction during deployment) is maintained by aligning a flat on the upper portion 58 of the curved cannula 50 to an alignment pin secured perpendicularly into the needle trocar 20 handle 24. Once the curved cannula 50 is secure, the straightening stylet 40 is removed, while the curved cannula 50 remains stationary within the trocar 20.

Referring to FIG. 4C, the curved stylet 60 is then straightened out by sliding the small tube 68 proximally to distally on its shaft towards the distal tip 64 or from the distal tip 64 proximally on its shaft towards the proximal end 62. Once the curved distal tip 66 is straightened out and fully retracted inside the small tube 68, the curved stylet 60 is inserted into the proximal aperture 53 of the curved cannula 50, which still resides inside the needle trocar 20. As the curved stylet 60 is advanced into the curved cannula 50, the small tube 68 is met by a stop 55 (see FIG. 4C). As the curved stylet 60 continues to advance the small tube 68 is held inside the handle of the curved cannula 50. This allows the curve of the stylet 60 to be exposed inside the curved cannula 50. To create the maximum force the curve of the two parts (50 & 60) must be aligned. To ensure alignment the cap on the curved stylet 60 has an alignment pin 70 which engages with an alignment notch on the proximal end 52 of the curved cannula 50.

Once the stylet 60 is fully seated and aligned with the curved cannula 50 the tip of the curved stylet 60 will protrude from the tip of the curved cannula 50 by about 1/16 to 3/16 inches. This protrusion will help to drive the curve in the direction of its orientation during deployment.

Referring now to FIG. 4D, with the curved stylet 60 and the curved cannula 50 engaged, the locking nut 58 at the top of the curved cannula 50 is rotated counter clockwise to allow the cannula 50 and curved stylet 60 to be advanced with relation to the needle trocar 20 such that the proximal end 52 abuts against 58, advancing the curved cannula 50 and curved stylet 60 beyond the distal opening of trocar 20 to generate a curved path in the cancellous bone region 124. As the curved cannula and stylet are advanced they will curve at a radius of 0.6 to 1.0 inches and arc to an angle between 5 and 90 degrees. Alternatively, as the curved cannula 50 and curved stylet 60 are advanced they will preferably curve at a radius of 0.4 to 1.0 inches through cancellous bone and arc to an angle between 5 and 110 degrees. Once the curved cannula 50 and curved stylet 60 are deployed to the intended angle, the locking nut at the top of the curved cannula 50 is engaged with the needle trocar 20 to stop any additional advancement of the curved stylet cannula assembly.

FIGS. 7A-7B illustrate the tip of the curved stylet 60, which has been formed with two angles. To help the curve deployment in the proper direction the curved section 66 of the curved stylet 60 is shaped in a predetermined orientation. The angle on the inside of the curve 72 is less than the angle on the outside of the curve 74. This disparity in angle helps the stylet cannula assembly 50 & 60 curve in the bone as bone pushes against outside curve face 74 ensuring the curve radius is maintained during deployment.

Figure 4E:
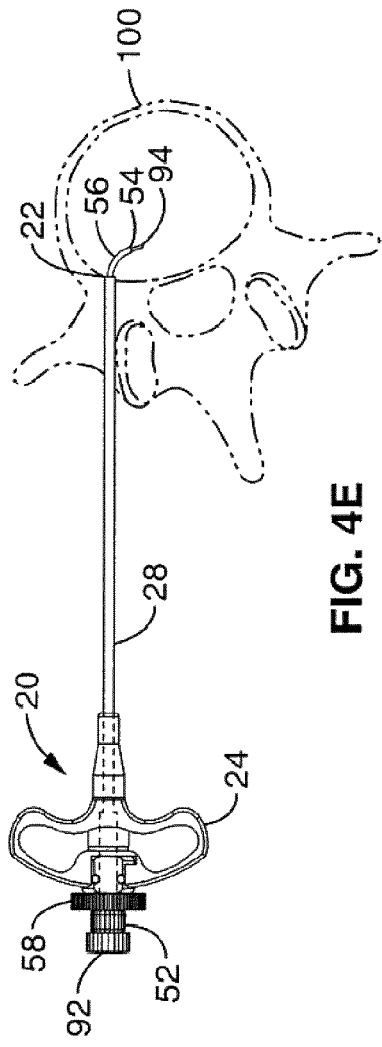

Referring now to FIG. 4E, the curved stylet 60 is then removed and replaced by the channeling stylet 90. The tip 94 of the channeling stylet 90 is advanced beyond the end 54 of the curved cannula 50 towards the intended target treatment zone.

Figure 4F:
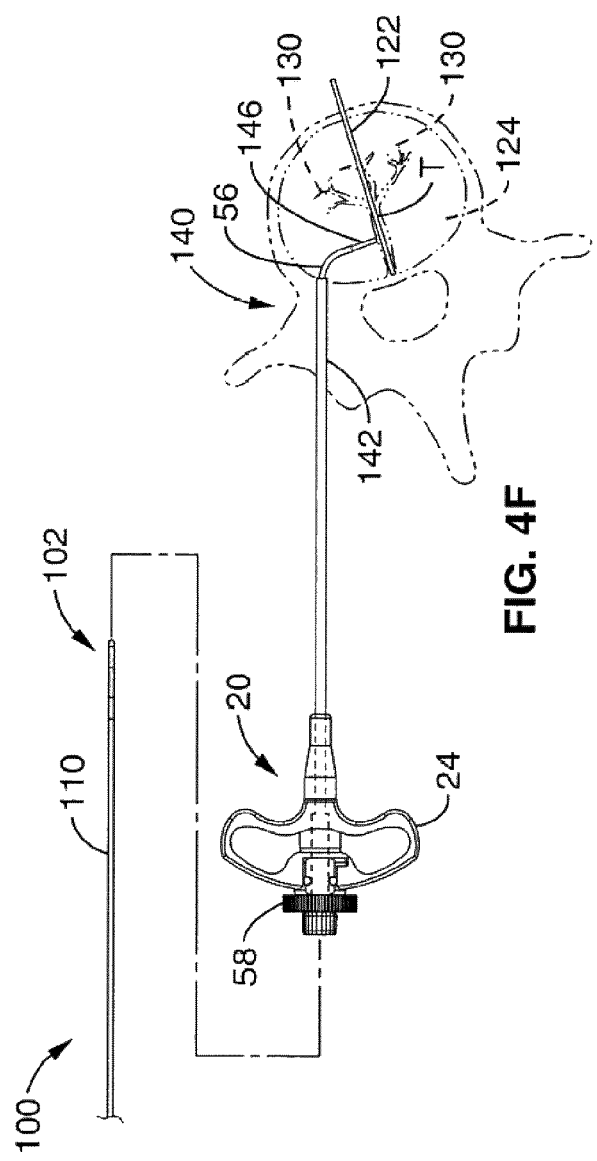

Referring now to FIG. 4F, once the channeling stylet 90 reaches the target treatment zone, it is removed creating a working channel 146. Channel 140 will generally have a first section 142 that crosses the cortical bone of the pedicle 138, followed by a curved path 144. These sections are occupied by curved cannula 50 such that a treatment device fed through the cannula 50 will have to follow the curve of the cannula 50 and not veer off in another direction. The channel may further comprise the linear extension 146 in the cancellous bone 124 to further advance the treatment device toward the treatment site T.

With the trocar 20 and curved cannula 50 still in place, a treatment device (e.g. treatment probe 100 shown in FIG. 2, with an active element 102 on the distal end 104 of elongate flexible catheter 110 is delivered to the target treatment location T to perform a localized treatment.

In a preferred embodiment, the active element 102 is delivered to the treatment site and activated to delivery therapeutic treatment energy. The treatment probe may comprise an RF delivery probe having bipolar electrodes 106 and 108 that deliver a therapeutic level of heating to stimulate or ablate the nerve 122.

It is appreciated that any number of treatment modalities may be delivered to the treatment site for therapeutic treatment. For example, treatment may be affected by monopolar or tripolar RF, ultrasound, radiation, steam, microwave, laser, or other heating means. Additionally, the treatment device may comprise a fluid delivery catheter that deposits an agent, e.g. bone cement, or other therapeutic agent, to the treatment site T. Alternatively, cryogenic cooling may be delivered for localized treatment of the BVN. Furthermore, treatment may be affected by any mechanical destruction and or removal means capable of severing or denervating the BVN. For example, a cutting blade, bur or mechanically actuated cutter typically used in the art of orthoscopic surgery may be used to affect denervation of the BVN.

In addition to or separate from treating the BVN, a sensor may be delivered to the region to preoperatively or postoperatively measure nerve conduction at the treatment region. In this configuration, the sensor may be delivered on a distal tip of a flexible probe that may or may not have treatment elements as well.

The goal of the treatment may be ablation, or necrosis of the target nerve or tissue, or some lesser degree of treatment to denervate the BVN. For example, the treatment energy or frequency may be just sufficient to stimulate the nerve to block the nerve from transmitting signal (e.g. signals indicating pain).

Once the treatment is complete, the probe 100 is withdrawn. The curved cannula 50 is then withdrawn into the needle trocar 20. The needle trocar 20 with the curved cannula 50 is then removed and the access site is closed as prescribed by the physician.

In the above system 10, the design of the curved sections 56 and 66 of the curved cannula 50 and curved stylet 60, respectively, is such that the flexible element (e.g. carrying the treatment device) can navigate through the angular range of deployment of the Nitinol tube of the curved cannula 50. The curved nitinol tube of the curved cannula 50 allows the flexible element to navigate through a curve within bone without veering off towards an unintended direction. Cancellous bone density varies from person to person. Therefore, creating a curved channel within varying density cancellous bone 124 will generally not predictably or accurately support and contain the treatment device as it tries to navigate the curved channel.

With the system 10 of the present invention, the treatment device 100 is deployed into the bone through the curved Nitinol tube of the curved cannula 50, which supports the element as it traverses through the curve. When it departs from the tube, it will do so in a linear direction along path 146 towards the target zone. This allows the user to predictably and accurately deploy the treatment device towards the target zone T regardless of the density of the cancellous bone.

In some embodiments, a radius of curvature that is smaller than that which can be achieved with a large diameter Nitinol tube may be advantageous. To achieve this, the curved tube of the curved cannula 50 may take one of several forms. In one embodiment, the tube 50 is formed from a rigid polymer that can be heat set in a particular curve. If the polymer was unable to hold the desired curve, an additional stylet (e.g. curved stylet 60) of Nitinol, or other appropriate material, may also be used in conjunction with the polymer tube to achieve the desired curve. This proposed combination of material may encompass and number or variety of materials in multiple different diameters to achieve the desired curve. These combinations only need to ensure that the final outside element (e.g. trocar 20) be "disengageable" from the internal elements and have an inner diameter sufficient to allow the desired treatment device 100 to pass to the treatment region T.

In an alternative embodiment, of the curved cannula 50 may comprise a Nitinol tube having a pattern of reliefs or cuts (not shown) in the wall of the tube (particularly on the outer radius of the bend). The pattern of cuts or reliefs would allow the tube to bend into a radius tighter than a solid tube could without compromising the integrity of the tubing wall.

FIG. 5 illustrates a second embodiment of the system or kit 200 of the present invention that may be used to reduce the number of steps required for the procedure. The second embodiment includes a needle trocar 20, straightening stylet 40, used with the needle trocar 20 and the curved cannula 50 to create the initial path through the soft tissue and cortical shell to allow access to the cancellous bone, curved stylet 60 used in conjunction with the curved cannula 50 to create the curved path within the bone/tissue, and channeling stylet 90 used to create a working channel for the probe beyond the end of the curved path created by the curved stylet.

In one method according to the present invention, the straightening stylet 40 is inserted into the curved cannula 50 and secured. In this embodiment, the straightening stylet 40 has a sharp tip 46 designed to penetrate bone. Once the straightening stylet 40 is secure and the curved cannula 50 is straight, they are inserted into the needle trocar 20 and secured. In this embodiment, the curved cannula 50 and straightening stylet 40 are inserted into the shaft 28 of the trocar 20 only as far as to have sharp tip 46 of the straightening stylet 40 protrude from the distal end 22 of the trocar 20. Proper alignment is maintained by aligning a flat on the upper portion of the curved cannula 50 with a pin secured perpendicularly into the needle trocar 20 handle.

Referring now to FIG. 6, once the curved cannula 50 is secure, the assembly (trocar 20, curved cannula 50, and straightening stylet 40) is advanced through soft tissue to the surface of the bone. After finding the proper alignment at the pedicle 138 of vertebrae 120, the assembly (trocar 20, curved cannula 50, and straightening stylet 40) is advanced through the cortical shell 128 and into the cancellous interior 124 of the bone.

After the proper depth is achieved, the straightening stylet 40 is removed. The curved stylet 60 is then straightened out by sliding the small tube 68 on its shaft towards the distal tip 64. The curved distal tip 66 is straightened out and fully retracted inside the small tube 68, and then the curved stylet 60 is inserted into the curved cannula 50 which still resides inside the needle trocar 20. Once the curved stylet 60 is inserted into the curved cannula 50, the small tube 68 is met by a stop 55 (see FIG. 4C). As the curved stylet 60 continues to advance, the small tube 68 is held inside the handle of the curved cannula 50. This allows the curve of the stylet 60 to be exposed inside the curved cannula 50.

To create the maximum force, it is preferred that the curve of the two parts (50 & 60) are aligned. To ensure alignment the cap on the curved stylet 60 has an alignment pin, which engages with a notch on the top of the curved cannula 50.

When the stylet 60 is fully seated and aligned with the curved cannula 50, the tip of the curved stylet 60 will protrude from the tip of the curved cannula 50 by about 1/16 to 3/16 inches. This protrusion will help to drive the curved cannula 50 in the direction of its orientation during deployment. Once the curved stylet 60 and the curved cannula 50 are engaged, the lock nut at the top of the curved cannula 50 is rotated counter clockwise to allow the cannula 50 and stylet 60 to be advanced with relation to the needle trocar 20 (as shown in FIG. 4D). As the curved cannula and stylet are advanced they generate a curved path toward the treatment location T. Once the curved cannula 50 and stylet 60 are deployed to the intended angle, the lock nut at the top of the curved cannula 50 is engaged with the needle trocar 20 to stop any additional advancement of the curved stylet cannula assembly.

The curved stylet 60 is then removed and replaced by the channeling stylet 90. The channeling stylet 90 is advanced beyond the end of the curved cannula 50 (see FIG. 4E) towards the intended target treatment zone creating a working channel for the active element to be inserted. Once the channeling stylet 80 reached the target treatment zone it is removed and replaced by the treatment device 100, which is delivered to the treatment site T and activated.

Once the treatment is complete, the treatment device 100 is withdrawn. The curved cannula 50 is then withdrawn into the needle trocar 20. The needle trocar 20 with the curved cannula 50 is then removed and the access site is closed as prescribed by the physician.

FIGS. 7A and 7B illustrate detail views of a Nitinol wire for the curved stylet 60 (proximal end not shown). The wire comprises a shaft 78 having constant diameter D and a length $L_s$ that may vary according to the application and desired depth to the treatment location. The wire has a preformed distal tip that is curved to have a radius r that redirects the distal tip 64 at an angle $\Theta$ with the shaft. As shown in FIG. 7A, angle $\Theta$ is shown to be approximately 110°. However, it is appreciated that the preformed tip may have an angle ranging from a few degrees (slight deflection off axis), to up to 180° (e.g. directing back toward the proximal end).

As shown in FIG. 7B detailing the distal tip 64, the tip may have a distal extension $L_T$ that extends away from the shaft 78. To promote channeling along a path that follows radius r, the distal tip 64 is configured with a dual-plane bevels 74 and 72. Plane 74 is offset at angle $\beta$, and plane 72 is offset at angle $\alpha$. This configuration of the leading-allows for the stylet and/or curved cannula to travel through bone in a path correlating to the specified curve in the stylet and/or cannula.

In the example illustrated in FIGS. 7A and 7B, the curved stylet 60 has a shaft length $L_s$ of approximately 3.6 in., diameter D of approximately 0.040 in., and a distal tip length $L_T$ of 0.125 in., radius r of 0.40 in., and angle $\beta=35°$ and angle $\alpha=31°$. It should be noted that the above dimensions are for illustration only, and may vary depending on the anatomy an tissue type.

It is appreciated that all the above embodiments may be provided as a kit of instruments to treat different regions of the body. For example, the location, orientation and angle of the treatment device with respect to the trocar 20 may be varied by providing a set of instruments at varying increments. This may be achieved by varying the curvature (56, 66) in the curved cannula 50 and curved stylet 60. The curvature may be varied by varying the radius of curvature r, the insertion depth (shaft length $L_s$ and tip length $L_T$, and/or the final exit angle $\Theta$ with respect to the trocar 20 central bore. Thus, the physician may select a different kit for treating a lumber spine segment as opposed to a cervical spine segment, as the anatomy will dictate the path that needs to be channeled.

Thus, when treating different spine segments, a set out of the kit may be selected to match the vertebra (or other region being treated). For example, delivering the treatment device at or near the BVN junction for a lumbar vertebra may have a different angle than for a cervical vertebra, and may vary from patient to patient. The set may be selected from the kit intraoperatively, or from a pre-surgery diagnostic evaluation (e.g. radiographic imaging of the target region).

It is appreciated that each of the instruments in the embodiments 100 and 200 detailed above may have any length, shape, or diameter desired or required to provide access to the treatment region (e.g. intraosseous nerve trunk) thereby facilitating effective treatment of the target region. For example, the size of the intraosseous nerve to be treated, the size of the passageway in the bone (e.g. pedicle 138) for accessing the intraosseous nerve, and the location of the bone, and thus the intraosseous nerve, are factors that that may assist in determining the desired size and shape of the individual instruments.

The systems 100, 200 described above may be used with a number of different treatment modalities for therapeutic treatment of the target region. For example, in one embodiment, it is desirable to operate the treatment device 100 in a manner that ablates the tissue of the target region (e.g. BVN) to produce as described in U.S. Pat. No. 6,699,242, herein incorporated by reference in its entirety.

In another embodiment, the treatment device is configured to deliver therapeutic treatment that is targeted to block nerve conduction without ablating the nerve, i.e. thermal treatment is delivered to the nerve (e.g. via thermal therapy, agent or the like) that results in denervation of the BVN without necrosis of tissue. This may be achieved via delivery of a lesser amount of energy or agent to the tissue site (either in the form of less exposure time, concentration, intensity, etc.) than is required for ablation, but an amount sufficient to achieve some amount of temporary or permanent denervation.

As can be seen, therefore, the present invention includes the following inventive embodiments among others:

1. A system for channeling a path into bone, comprising: a trocar having a central channel and opening at its distal tip; and a curved cannula sized to be received in said central channel and delivered to said distal opening; the curved cannula having a deflectable tip with a preformed curve such that the tip straightens while being delivered through the trocar and regains its preformed curve upon exiting and extending past the distal opening of the trocar to generate a curved path in the bone corresponding to the preformed curve of the deflectable tip; wherein the curved cannula comprises a central passageway having a diameter configured allow a treatment device to be delivered through the central passageway to a location beyond the curved path.

2. A system as recited in embodiment 2, further comprising: a straight stylet configured to be installed in the trocar; the straight stylet comprising a sharp distal tip that is configured to extend beyond the distal opening of the trocar to pierce the bone as the trocar is being delivered to a treatment location within the bone.

3. A system as recited in embodiment 2, further comprising: a straightening stylet configured to be installed in the curved cannula; the straightening stylet comprising a rigid construction configured to straighten the distal tip of the curved cannula when positioned in the trocar.

4. A system as recited in embodiment 3, wherein the straightening stylet further comprises a sharp distal end to pierce the bone; and wherein the straightening stylet and curved cannula are configured to be installed in the trocar in place of the straight stylet as the trocar is delivered into the bone.

5. A system as recited in embodiment 1, further comprising: a curved stylet having an outer radius sized to fit within the central passageway of the curved cannula; wherein the curved stylet is configured to be installed in the curved cannula while the curved cannula is extended past the distal opening of the trocar, the curved stylet configured to block the distal opening of the curved cannula while being delivered into the bone.

6. A system as recited in embodiment 5, wherein the curved stylet has a curved distal end corresponding to the curve of the curved cannula.

7. A system as recited in embodiment 5, wherein the curved stylet has a sharp distal tip configured to extend past the curved cannula to pierce the bone as the cannula is delivered past the distal opening of the trocar.

8. A system as recited in embodiment 7, wherein the curved stylet and the curved cannula have mating proximal ends that align the curve of the curved stylet with the curve of the curved cannula.

9. A system as recited in embodiment 5, further comprising a straight channeling stylet configured to be installed in the cannula after removing the curved stylet; wherein the straight channeling stylet is flexibly deformable to navigate the curved cannula yet retain a straight form upon exiting the curve cannula; wherein straight channeling stylet has a length longer than the curved cannula such that it creates a linear path beyond the distal end of the curved cannula when fully extended.

10. A method for channeling a path into bone to a treatment location in the body of a patient, comprising: inserting a trocar into a region of bone near the treatment location; the trocar having a central channel and opening at its distal tip; and delivering a cannula through said central channel and to said distal opening; wherein the cannula comprises a deflectable tip with a preformed curve such that the tip straightens while being delivered through the trocar and regains its preformed curve upon exiting the trocar; extending the cannula past the distal opening of the trocar to generate a curved path in the bone corresponding to the preformed curve of the deflectable tip; delivering a treatment device through a central passageway in said cannula having to the treatment location beyond the curved path.

11. A method as recited in embodiment 10, wherein inserting a trocar into a region of bone comprises inserting a stylet into the trocar such that the stylet extends beyond the distal opening of the trocar; and inserting the stylet and trocar simultaneously into the region of bone such that the stylet pierces the bone as the trocar is being delivered to a treatment location.

12. A method as recited in embodiment 10, wherein delivering a cannula through the central channel comprises: inserting a straightening stylet into the central passageway of the cannula; the straightening stylet comprising a rigid construction configured to straighten the curved distal tip of the cannula; and inserting the straightening stylet and straightened cannula simultaneously into the trocar.

13. A method as recited in embodiment 12, wherein the straightening stylet further comprises a sharp distal end to pierce the bone; and wherein the straightening stylet and cannula are installed simultaneously along with the trocar as the trocar is delivered into the bone.

14. A method as recited in embodiment 10, wherein extending the cannula past the distal opening comprises: inserting a curved stylet into the central passageway of the curved cannula such that a distal tip of the curved stylet extends to at least the distal opening of the curved cannula; simultaneously extending the curved cannula and curved stylet from the distal end of the trocar such that the curved stylet blocks the distal opening of the curved cannula while being delivered into the bone.

15. A method as recited in embodiment 14, wherein the curved stylet has a curved distal end corresponding to the curve of the curved cannula; and wherein the curved stylet reinforces the curved shape of the curved cannula as the curved cannula is extended past the distal opening of the trocar.

16. A method as recited in embodiment 14, wherein the curved stylet has a sharp distal tip; wherein curved stylet is advanced within the central passageway so that the curved stylet extends past the distal opening of the curved cannula such that the curved stylet pierces the bone as the cannula is delivered past the distal opening of the trocar.

17. A method as recited in embodiment 14, further comprising: removing the curved stylet from the curved cannula; inserting a straight channeling stylet into the curved distal end of the cannula; wherein the straight channeling stylet is flexibly deformable to navigate the curved cannula yet retain a straight form upon exiting the curved cannula; wherein the straight channeling stylet is longer than the curved cannula to create a linear channel beyond the distal tip of the curved cannula.

18. A method as recited in embodiment 10, wherein the trocar is inserted through a cortical bone region and into a cancellous bone region of a vertebrae, and wherein the curved cannula is extended though at least a portion of the cancellous bone region to a location at or near the treatment location.

19. A method as recited in embodiment 18, wherein the treatment location comprises a BVN of the vertebrae, the method further comprising: delivering treatment to the treatment location to denervate at least a portion of the BVN.

20. A method as recited in embodiment 19, wherein denervating a portion of the BVN comprises delivering focused, therapeutic heating to an isolated region of the BVN.

21. A method as recited in embodiment 19, wherein denervating a portion of the BVN comprises delivering an agent to the treatment region to isolate treatment to that region.

22. A method as recited in embodiment 19, wherein the treatment is focused on a location of the BVN that is downstream of one or more branches of the BVN.

23. A kit for channeling a path into bone, comprising: a trocar having a central channel and opening at its distal tip; and a cannula selected from a set of cannulas sized to be received in said central channel and delivered to said distal opening; the cannula having a deflectable distal tip with a preformed curve such that the tip straightens while being delivered through the trocar and regains its preformed curve upon exiting and extending past the distal opening of the trocar to generate a curved path in the bone corresponding to the preformed curve of the deflectable tip; wherein the cannula comprises a central passageway having a diameter configured allow a treatment device to be delivered through the central passageway to a location beyond the curved path; wherein the set of cannulas comprises one or more cannulas that have varying preformed curvatures at the distal tip.

24. A kit as recited in embodiment 23, wherein the one or more cannulas have a varying preformed radius at the distal tip.

25. A kit as recited in embodiment 23, wherein the one or more cannulas each have distal tips that terminate at varying angles with respect to the central channel of the trocar.

26. A kit as recited in embodiment 25, wherein the angle of the distal tip with respect to the central channel of the trocar varies from approximately 45° to approximately 110°.

27. A kit as recited in embodiment 23, further comprising: a straight stylet configured to be installed in the trocar; the straight stylet comprising a sharp distal tip that is configured to extend beyond the distal opening of the trocar to pierce the bone as the trocar is being delivered to a treatment location within the bone.

28. A kit as recited in embodiment 23, further comprising: a set of curved stylets having an outer radius sized to fit within the central passageway of the curved cannula; wherein each curved stylet is configured to be installed in the curved cannula while the curved cannula is extended past the distal opening of the trocar; wherein the curved stylet configured to block the distal opening of the curved cannula while being delivered into the bone; and wherein each curved stylet has a varying a curved distal end corresponding to the curve of a matching curved cannula in the set of curved cannulas.

29. A kit as recited in embodiment 28, wherein the curved stylet has a sharp distal tip configured to extend past the curved cannula to pierce the bone as the cannula is delivered past the distal opening of the trocar.

30. A kit as recited in embodiment 28, wherein the curved stylet and the curved cannula have mating proximal ends that align the curve of the curved stylet with the curve of the curved cannula.

31. A kit as recited in embodiment 28, further comprising a set of straight channeling stylets; wherein one of the set of stylets is configured to be installed in the cannula after removing the curved stylet; wherein the straight channeling stylet is flexibly deformable to navigate the curved cannula yet retain a straight form upon exiting the curve cannula; wherein each of the straight channeling stylets has a varying length longer than the curved cannula such that the straight channeling stylet creates a predetermined-length linear path beyond the distal end of the curved cannula when fully extended.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for channeling a path into bone to a treatment location in a body of a patient, comprising:
    inserting an introducer into a region of the bone near the treatment location, the introducer having a central channel and an opening at a distal tip of the introducer;
    delivering a curved cannula through said central channel of said introducer to said opening,
    wherein a proximal portion of the curved cannula comprises a locking nut to control advancement of the curved cannula with respect to the introducer,
    wherein the curved cannula comprises a deflectable distal tip having a preformed curve such that the deflectable distal tip straightens while being delivered through the introducer and transitions to a curved configuration upon exiting the introducer,
    wherein the deflectable distal tip of the curved cannula is configured to arc to an angle of between 5 degrees and 90 degrees;
    moving the locking nut to a position such that the locking nut is in contact with a proximal end of the curved cannula, thereby allowing the deflectable distal tip of the curved cannula to be advanced past the opening at the distal tip of the introducer and to transition to the curved configuration;
    extending the curved cannula past the opening at the distal tip of the introducer to generate a curved path in the bone corresponding to the preformed curve of the deflectable distal tip;
    inserting a channeling stylet into the curved cannula,
    wherein the channeling stylet is flexibly deformable to navigate the curved cannula yet rigid enough to retain a straight form upon exiting the deflectable distal tip of the curved cannula;
    creating a linear channel starting at a distal end of the curved path formed by the curved cannula by extending a distal end of the channeling stylet out of the deflectable distal tip of the curved cannula;
    removing the channeling stylet from the curved cannula; and
    delivering a treatment device through said curved cannula to the treatment location through the linear channel.

2. The method of claim 1, wherein inserting the introducer into the region of bone comprises:
    inserting a stylet into the introducer such that the stylet extends beyond the opening of the introducer;
    inserting the stylet and the introducer simultaneously into the region of bone such that the stylet pierces the bone as the introducer is being delivered to the treatment location.

3. The method of claim 1, wherein delivering the curved cannula through the central channel comprises:
    inserting a straightening stylet into a central passageway of the curved cannula; the straightening stylet comprising a rigid construction configured to straighten the deflectable distal tip of the curved cannula;
    inserting the straightening stylet and the curved cannula simultaneously into the introducer; and
    removing the straightening stylet from the curved cannula.

4. The method of claim 3:
    wherein the straightening stylet further comprises a sharp distal end to pierce the bone;
    wherein the sharp distal end extends beyond a distal opening of the curved cannula; and
    wherein the straightening stylet and the curved cannula are installed simultaneously along with the introducer as the introducer is delivered into the bone.

5. The method of claim 1, wherein extending the curved cannula past the opening at the distal tip of the introducer comprises:
    inserting a curved stylet into a central passageway of the curved cannula such that a distal tip of the curved stylet extends to at least a distal opening of the curved cannula; and
    simultaneously extending the curved cannula and the curved stylet from the distal end of the introducer such that the curved stylet blocks the distal opening of the curved cannula while being delivered into the bone.

6. The method of claim 5, further comprising removing the curved stylet from the curved cannula.

7. The method of claim 1, wherein the treatment location corresponds to a location of a portion of a basivertebral nerve of a vertebra, the method further comprising:
 delivering treatment to the treatment location to denervate at least the portion of the basivertebral nerve.

8. The method of claim 7, wherein denervating the portion of the basivertebral nerve comprises delivering focused, therapeutic heating to the treatment location.

9. The method of claim 7, wherein denervating the portion of the basivertebral nerve comprises delivering an agent to the treatment location.

10. The method of claim 7, wherein the treatment location corresponds to the location of the portion of the basivertebral nerve that is downstream of one or more branches of the basivertebral nerve.

11. The method of claim 7, wherein delivering treatment to the treatment location to denervate at least the portion of the basivertebral nerve comprises delivering radiofrequency energy to the treatment location to denervate at least the portion of the basivertebral nerve.

12. The method of claim 7, wherein delivering treatment to the treatment location to denervate at least the portion of the basivertebral nerve comprises delivering ultrasonic energy to the treatment location to denervate at least the portion of the basivertebral nerve.

13. A method for channeling a path into vertebral bone to a treatment location in a body of a patient, comprising:
 providing an energy delivery system, said energy delivery system comprising an introducer, a curved cannula, a channeling stylet, and an energy delivery probe;
 inserting the introducer through a pedicle and into a cancellous bone region of the vertebral bone near the treatment location,
 wherein the introducer has a central channel along its longitudinal axis and an axial opening at a distal tip of the introducer;
 delivering the curved cannula through said central channel of said introducer to said axial opening at the distal tip of the introducer,
 wherein a proximal end of the curved cannula comprises a locking nut to control advancement of the curved cannula with respect to the introducer,
 wherein the curved cannula comprises a deflectable distal tip having a preformed curved configuration such that the deflectable distal tip straightens while being delivered through the central channel of the introducer and curves again upon exiting the axial opening of the introducer;
 extending the curved cannula past the axial opening at the distal tip of the introducer to generate a curved path toward the treatment location corresponding to the preformed curved configuration of the deflectable distal tip of the curved cannula,
 wherein the curved cannula is extended through at least a portion of the cancellous bone region to a location near the treatment location,
 wherein the deflectable distal tip of the curved cannula is configured to arc to an angle between 5 degrees and 110 degrees;
 creating a linear channel starting at a distal end of the curved path formed by the curved cannula by inserting the channeling stylet within the curved cannula and extending a distal end of the channeling stylet out of the deflectable distal tip of the curved cannula,
 wherein the channeling stylet is flexibly deformable to navigate the curved cannula yet rigid enough to retain a straight form upon exiting the deflectable distal tip of the curved cannula;
 removing the channeling stylet from the curved cannula;
 delivering the energy delivery probe through a central passageway in said curved cannula to the treatment location through the linear channel; and
 activating the energy delivery probe at the treatment location to deliver energy to the treatment location.

14. The method of claim 13, wherein the treatment location comprises an intraosseous nerve of the vertebral bone.

15. The method of claim 13, wherein the treatment location comprises a basivertebral nerve of the vertebral bone.

16. The method of claim 15, wherein the energy delivery probe comprises a radiofrequency ablation probe and wherein the step of activating the energy delivery probe at the treatment location to deliver energy to the treatment location comprises applying radiofrequency energy sufficient to denervate at least a portion of the basivertebral nerve at the treatment location.

17. The method of claim 15, wherein the energy delivery probe comprises an ultrasonic ablation probe and wherein the step of activating the energy delivery probe at the treatment location to deliver energy to the treatment location comprises applying ultrasonic energy sufficient to denervate at least a portion of the basivertebral nerve at the treatment location.

18. The method of claim 15, wherein the treatment location is posterior to a basivertebral nerve junction.

19. The method of claim 13, wherein the step of inserting the introducer through the pedicle and into the cancellous bone region of the vertebral bone near the treatment location comprises:
 inserting a stylet into the introducer such that the stylet extends beyond the axial opening of the introducer; and
 inserting the stylet and the introducer simultaneously into the vertebral bone such that the stylet pierces cancellous bone within the cancellous bone region as the introducer is being delivered toward the treatment location.

20. The method of claim 13, wherein the step of extending the curved cannula past the axial opening at the distal tip of the introducer comprises:
 inserting a curved stylet into the central passageway of the curved cannula such that a distal tip of the curved stylet extends to at least a distal opening of the curved cannula; and
 simultaneously extending the curved cannula and the curved stylet from the distal end of the introducer such that the curved stylet blocks the distal opening of the curved cannula while being delivered into the vertebral bone.

\* \* \* \* \*

UNITED STATES PATENT AND TRADEMARK OFFICE
CERTIFICATE OF CORRECTION

PATENT NO. : 9,039,701 B2  
APPLICATION NO. : 13/963767  
DATED : May 26, 2015  
INVENTOR(S) : Pellegrino et al.

Page 1 of 1

It is certified that error appears in the above-identified patent and that said Letters Patent is hereby corrected as shown below:

In the claims

Column 17 at line 58, Claim 13, after "angle" insert --of--.

Signed and Sealed this  
Third Day of May, 2016

Michelle K. Lee  
*Director of the United States Patent and Trademark Office*